United States Patent
Hockett et al.

(10) Patent No.: US 7,096,057 B2
(45) Date of Patent: Aug. 22, 2006

(54) METHOD AND APPARATUS FOR INTRACORPOREAL MEDICAL IMAGING USING A SELF-TUNED COIL

(75) Inventors: Frank Hockett, St. Charles, MO (US); Samuel A. Wickline, St. Louis, MO (US); Xin Yu, St. Louis, MO (US)

(73) Assignee: Barnes Jewish Hospital, St. Louis, MO (US)

( * ) Notice: Subject to any disclaimer, the term of this patent is extended or adjusted under 35 U.S.C. 154(b) by 461 days.

(21) Appl. No.: 10/210,931

(22) Filed: Aug. 2, 2002

(65) Prior Publication Data

US 2004/0024301 A1 Feb. 5, 2004

(51) Int. Cl.
*A61B 5/05* (2006.01)
(52) U.S. Cl. ...................... 600/422; 600/410
(58) Field of Classification Search ............... 600/422, 600/423, 407, 421, 410, 411
See application file for complete search history.

(56) References Cited

U.S. PATENT DOCUMENTS

| | | | |
|---|---|---|---|
| 4,932,411 A | | 6/1990 | Fritschy et al. |
| 5,095,911 A | | 3/1992 | Pomeranz |
| 5,235,283 A | * | 8/1993 | Lehne et al. ............... 324/318 |
| 5,699,801 A | | 12/1997 | Atalar et al. |
| 5,715,822 A | | 2/1998 | Watkins et al. |
| 5,928,145 A | | 7/1999 | Ocali et al. |
| 5,938,609 A | | 8/1999 | Pomeranz |
| 6,050,942 A | * | 4/2000 | Rust et al. .................. 600/437 |
| 6,078,831 A | | 6/2000 | Belef et al. |
| 6,171,240 B1 | | 1/2001 | Young et al. |
| 6,248,076 B1 | | 6/2001 | White et al. |
| 6,261,246 B1 | | 7/2001 | Pantages et al. |
| 6,263,229 B1 | | 7/2001 | Atalar et al. |
| 6,275,722 B1 | | 8/2001 | Martin et al. |
| 6,453,189 B1 | | 9/2002 | Gilderdale |
| 6,459,921 B1 | | 10/2002 | Belef et al. |

(Continued)

FOREIGN PATENT DOCUMENTS

EP 0 673 621 9/1995

(Continued)

OTHER PUBLICATIONS

Patent Cooperation Treaty; International Search Report; Dec. 5, 2003.

(Continued)

*Primary Examiner*—Daniel Robinson
(74) *Attorney, Agent, or Firm*—Thompson Coburn LLP

(57) ABSTRACT

Disclosed herein is an RF probe for use with a medical imaging apparatus, the probe comprising an intracorporeal self-tuned resonator coil for receiving a signal indicative of an image of an interior portion of a body. The resonator coil is preferably coupled to a transmission medium having a characteristic impedance such that the resonator coil is substantially self-matching with the transmission medium's characteristic impedance. Preferably the resonator coil comprises an open wound conductor having a plurality of turns. The length of the resonator coil can be used to tune the resonator coil to a desired frequency, such as the Larmour frequency. Further, a return lead of the transmission medium is preferably coupled to an end of the conductor, and a signal lead of the transmission medium is preferably coupled to a point on the winding, thereby defining a turns ratio for the resonator coil. The turns ratio of the resonator coil can be used to match the resonator coil to the characteristic impedance of the transmission medium. Because the resonator coil of the present invention is self-tuning and self-matching, it avoids the use of bulky and relatively expensive tuning and matching circuits.

30 Claims, 21 Drawing Sheets

$$f = \frac{1}{2\pi\sqrt{L_R C_D}}$$

U.S. PATENT DOCUMENTS 6,529,760 B1 3/2003 Pantages et al.
2001/0056232 A1 12/2001 Lardo et al.

FOREIGN PATENT DOCUMENTS

JP 06 070902 3/1994

OTHER PUBLICATIONS

Patent Abstracts of Japan for JP 06 070902; Jun. 16, 1994; vol. 18, No. 316.

Hockett et al.; *Design of a Self-Tuned RF Resonator for Use as an Intravenous Catheter*, Proceedings of the International Society for Magnetic Resonance in Medicine, Eleventh Scientific Meeting; Jul. 10, 2003; p. 2398; Toronto, Canada.

Quick et al.; *Single-Loop Coil Concepts for Intravascular Magnetic Resonance Imaging*; Magnetic Resonance in Medicine; 1999; pp. 751-758; vol. 41, No. 4; Academic Press; Duluth, Minnesota.

Rivas et al.; *In Vivo Real-Time Intravascular MRI*; Journal of Cardiovascular Magnetic Resonance; 2002; pp. 223-232; vol. 4, No. 2; United States.

Elgort et al.; Intravascular Catheter Tracking with Adaptive Imaging Parameters; *Journal of Cardiovascular Magnetic Resonance*; 2003; vol. 5, pp. 66-67.

Hillenbrand et al.; A Switchable Multi-Coil Array Optimized for Endovascular Procedures and High Resolution Vessel Wall Imaging; *Journal of Cardiovascular Magnetic Resonance*; 2003; vol. 5; pp. 62-64.

Wong et al.; Innovative Coil Design for Minimally Invasive Device Tracking Applications; *Journal of Cardiovascular Magnetic Resonance*; 2003; vol. 5; pp. 194-196.

Wong et al.; Simulations for Optimization of Design Parameters for Intravascular Imaging Microcoil Construction; *Journal of Cardiovascular Magnetic Resonance*; 2003; vol. 5; pp. 41-43.

Ocali et al.; *Intravascular Magnetic Resonance Imaging Using a Loopless Catheter Antenna*; Magnetic Resonance in Medicine, vol. 37, pp. 112-118, 1997.

Quick et al.; *Single-Loop Coil Concepts for Intravascular Magnetic Resonance Imaging*; Magnetic Resonance in Medicine, vol. 41; pp. 751-758, 1999.

Rivas et al.; *In Vivo Real-Time Intravascular MRI*; Journal of Cardiovascular Magnetic Resonance, vol. 4, No. 2, pp. 223-232, 2002.

The Basics of MRI, Chapter 9, Imaging Hardware; downloaded from http://www.cis.rit.edu/htbooks/mri/chap-9/chap-9.htm on May 28, 2002.

RF and Gradient Coils; downloaded from http://www.mritutor.org/mritutor/coils.htm on May 29, 2002.

\* cited by examiner

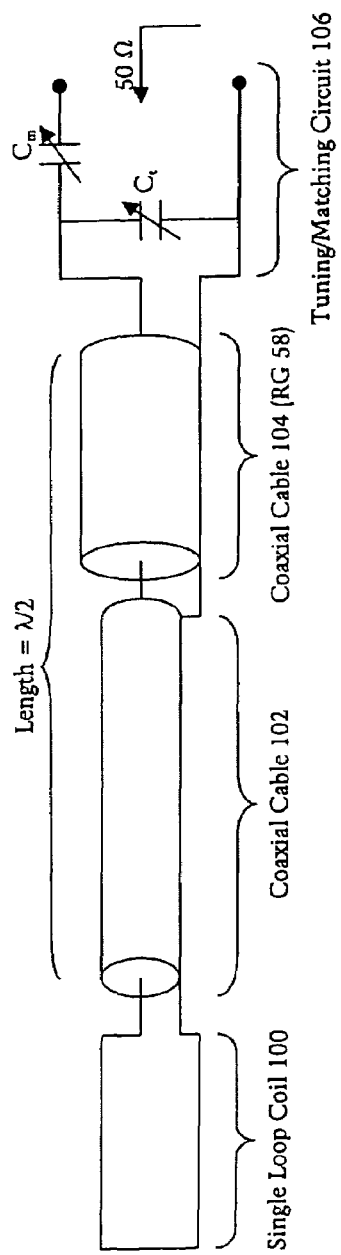
Figure 1: PRIOR ART
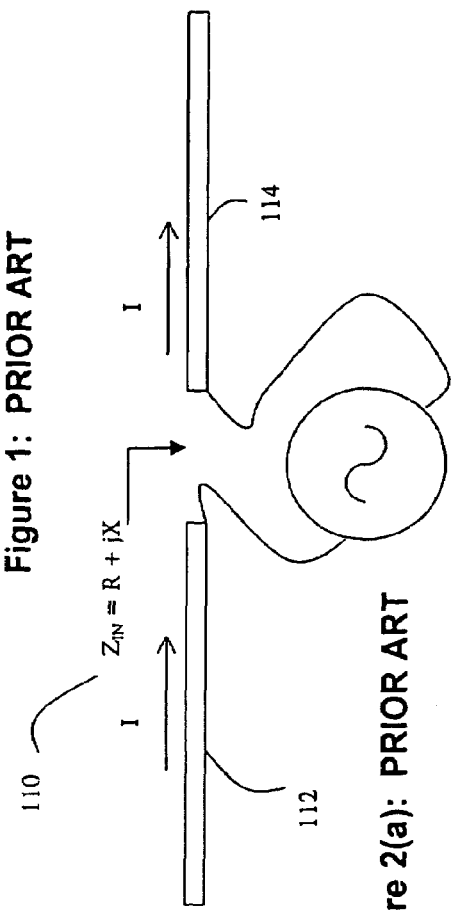
Figure 2(a): PRIOR ART
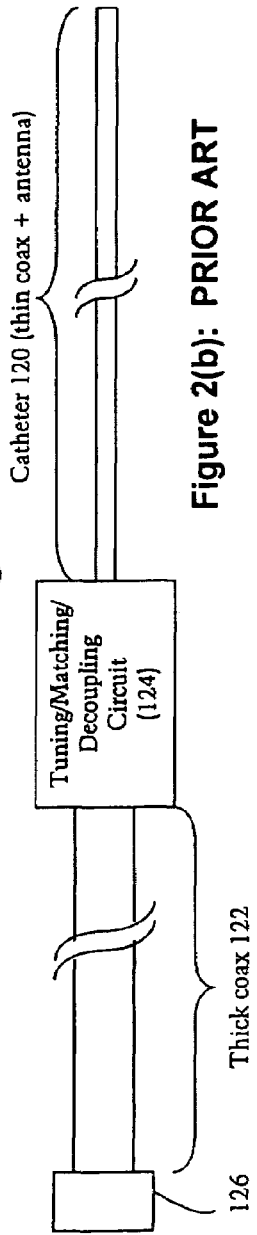
Figure 2(b): PRIOR ART

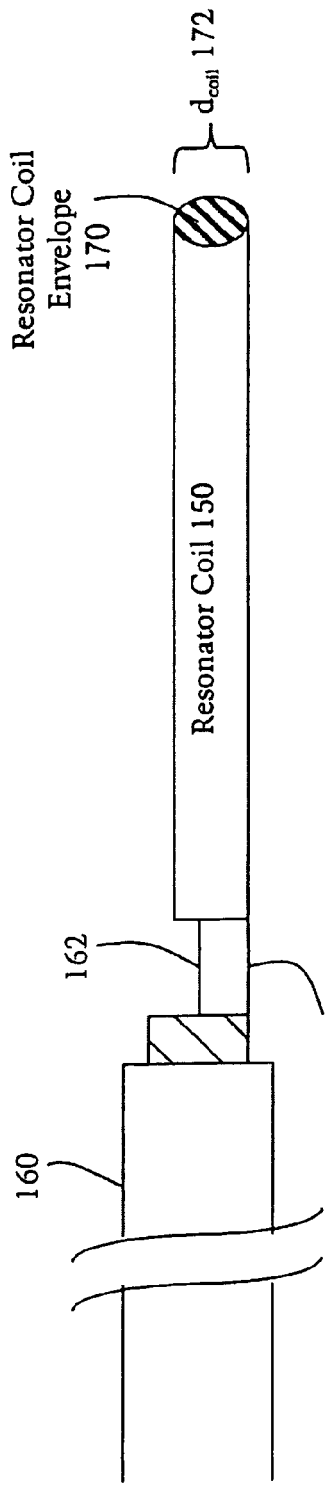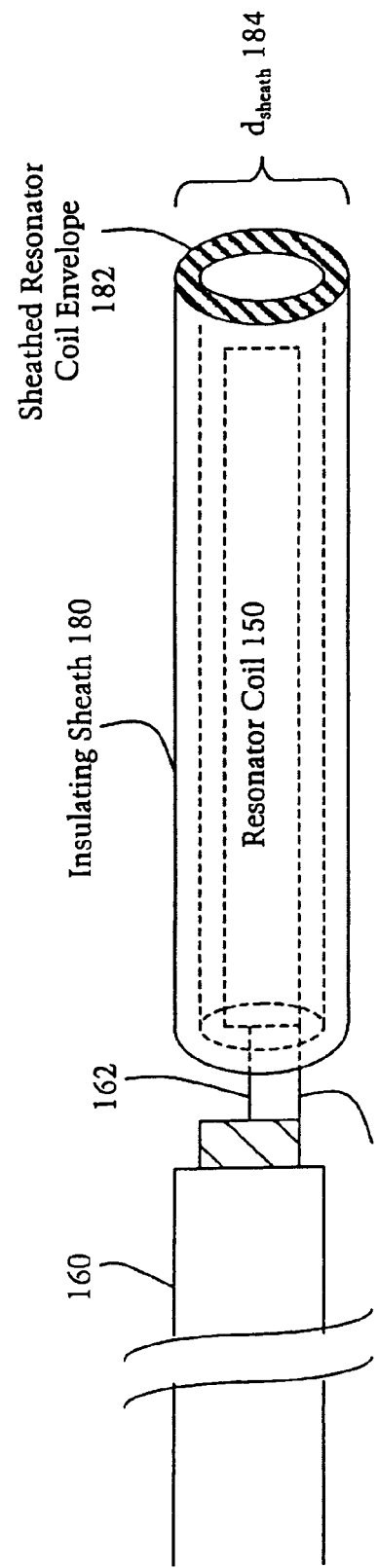

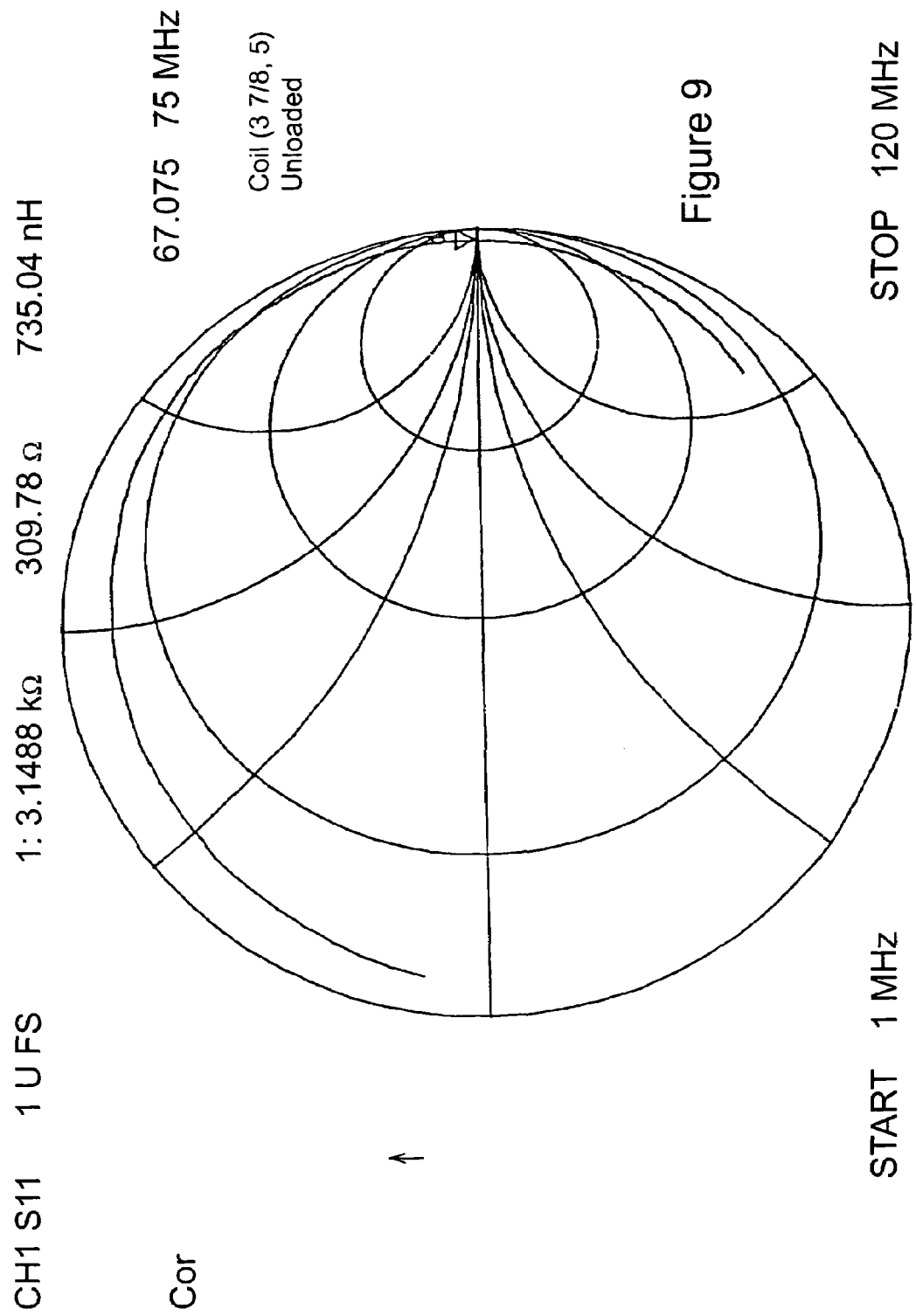

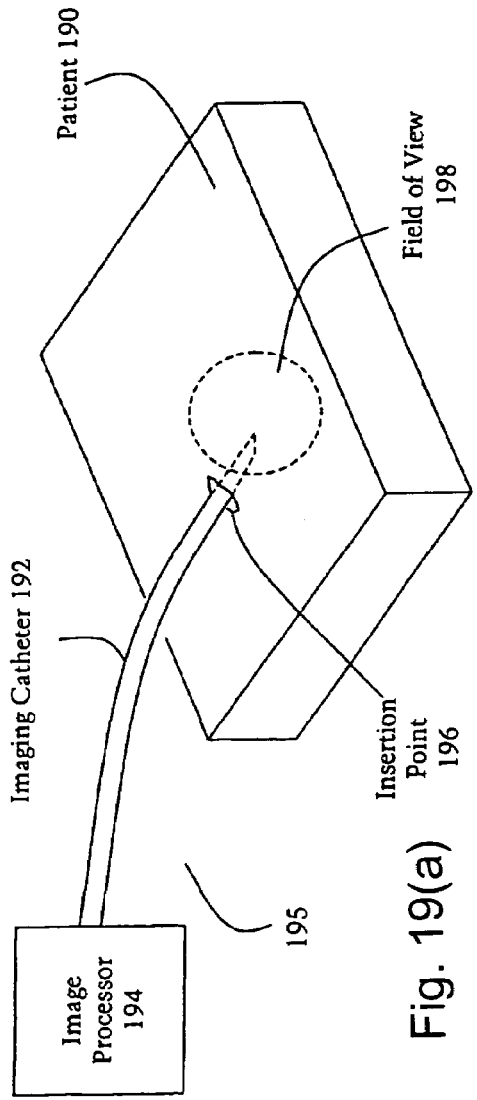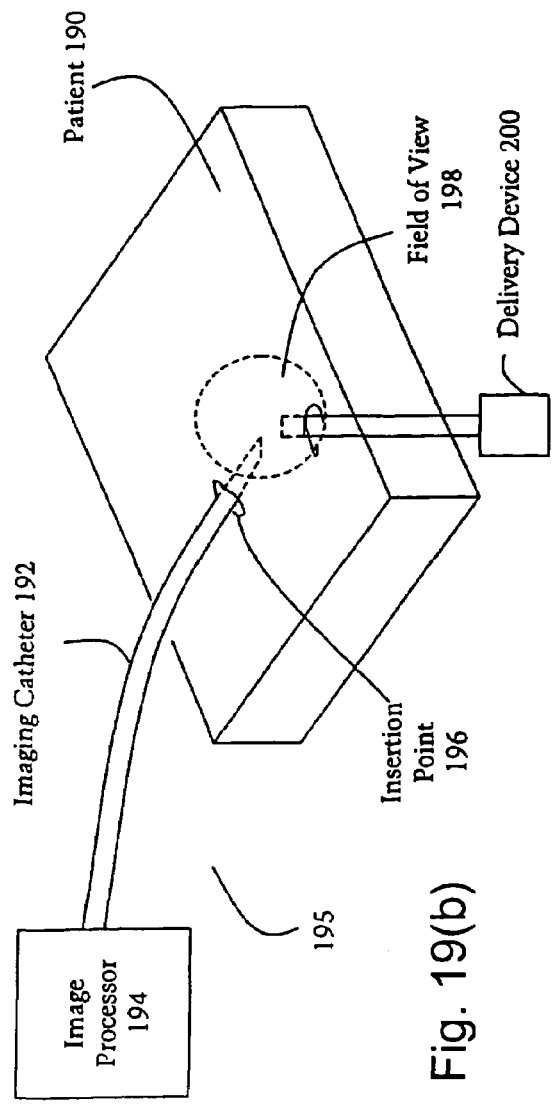
Fig. 19(a)
Fig. 19(b)

METHOD AND APPARATUS FOR INTRACORPOREAL MEDICAL IMAGING USING A SELF-TUNED COIL

FIELD OF THE INVENTION

The present invention relates to generating medical images of an internal portion of the body through the use of an imaging probe inserted into the body. More particularly, the present invention relates to an improved intravascular RF probe used in conjunction with magnetic resonance imaging (MRI).

BACKGROUND OF THE INVENTION

MRI imaging has become a widely-used and well-known imaging modality for generating images of interior portions of the human body. Because those of ordinary skill in the art are quite familiar with the basic concepts of MRI, those concepts need only be briefly set forth as background for the invention.

Toward that end, as is well-known, MRI machines are used to create images of interior portions of the body. In doing so, an MRI machine applies a magnetic field to at least a portion of the body to be imaged. A typical magnetic field strength is 1.5 T, although other field strengths are used (commonly in the range of 0.5 T–3.0 T). Thereafter, localized gradients are created in the magnetic field, and RF pulses are applied to a target area representing the portion of the body for which an image is desired. A typical frequency for the RF pulse is the Larmour frequency (around 63 MHz for protons in a magnetic field of 1.5 T). Protons in the target area absorb energy from the RF pulse in an amount sufficient to change their spin direction. Once the RF pulse is turned off, the protons release excess stored energy as they return to their natural alignment in the magnetic field. When releasing this stored energy, signals are created that are indicative of an image of the target area. When properly sensed, such signals can be processed by a computer to generate an MR image of the target area.

It is known in the art to receive such signals through the use of an intracorporeal RF probe (also referred to as an RF receiver). When disposed in the body proximate to the target area, such RF probes are capable of sensing the proton emissions and providing the sensed signal to the image generating computer system by way of a transmission medium such as a coaxial cable. Because such probes may be inserted into the body through very small openings, it is important that those receivers have as small of a mechanical envelope as possible.

Also, it is important that the receiver coil resonate (i.e., efficiently store energy) at the Larmour frequency. To resonate a particular frequency f, the inductive components (L) and capacitive components (C) of the receiver coil should satisfy the following equation:

$$f = \frac{1}{2\pi\sqrt{LC}}$$

The RF probes in prevalent use for MR imaging can be grouped into two basic categories (1) an elongated coil with a thin cross section, and (2) a loopless antenna (dipole) consisting of a single thin wire. An example of an elongated coil design for an RF receiver is described by Quick et al. in *Single-Loop Coil Concepts for Intravascular Magnetic Resonance Imaging*, Magnetic Resonance in Medicine, vol. 41, pp. 751–758 (1999), the entire disclosure of which is hereby incorporated by reference. An example of a loopless antenna design is described by Ocali and Atalar in *Intravascular Magnetic Resonance Imaging Using a Loopless Catheter Antenna*, Magnetic Resonance in Imaging, vol. 37, pp. 112–118 (1997), the entire disclosure of which is hereby incorporated by reference. Other coil examples are Helmholtz coils (which typically consist of two single loop coils in parallel) and flat coils.

FIG. 1 illustrates an exemplary prior art coil receiver assembly. A single loop coil 100 senses the signal emitted by the target area responsive to the RF pulses. Both coil 100 and thin coaxial cable 102 can be disposed inside the body of the patient. The signal passes from coil 100 through thin coaxial cable 102 to thicker coaxial cable 104, which may be RG 58 cable or the like. Together the thin and thick coaxial cables 102 and 104 have a length of $\lambda/2$ and form part of a tuned resonance circuit. The coil receiver assembly also includes an external tuning/matching circuit 106 as shown, wherein variable tuning capacitor $C_t$ forms a resonant circuit with the inductance of the coil 100 and cables 102 and 104, and variable matching capacitor $C_m$ matches the input impedance of the resonance circuit with that of the receiver (50 $\Omega$).

FIGS. 2(a) and 2(b) illustrate an exemplary prior art antenna receiver assembly. Dipole antenna 110 is shown in FIG. 2(a). The dipole antenna 110 is formed of two separated conductors 112 and 114. As the current path is not complete, charge oscillates between the two tips of the conductors 112 and 114. When implemented, the antenna 110 is coupled with thin coaxial cable and disposed within a catheter 120. Catheter 120 may be inserted within the body proximate to the target area for imaging thereof. For satisfactory quality of performance, the input impedance of the antenna 110 ($Z_{IN}$) must be matched with the characteristic impedance of coaxial cable 122 shown in FIG. 2(b). Also, to avoid interference caused by antenna resonation, detuning is needed to electronically damp the receiver's resonance by presenting the coaxial cable to the antenna as a large magnitude impedance. For these purposes, external tuning/matching/decoupling circuit 124 is provided to link the catheter 120 with coaxial cable 122 (which itself terminates at connector 126).

Such prior art receiver assemblies suffer from various shortcomings, namely (1) the single loop coil design exemplified by FIG. 1 works well for near field resolution but not for far field resolution (due to field cancellation occurring at a relatively short distance from the loop)—the near field and far field pertaining to the physical location of the imaging field relative to the receiver, (2) the antenna design exemplified by FIGS. 2(a) and 2(b) works well for far field resolution but not for near field resolution (as determined by the device's geometry which defines a near/far transition zone), (3) each design requires the use of bulky and relatively expensive external matching circuits and tuning circuits, and (4) the coil design of FIG. 1 allows heat to build up as current passes through the coil. While Helmholtz coils and flat coils do not suffer from troubling near/far field transition zones, those coils require the use of external matching and tuning circuits.

Additional coil designs are shown in the article Rivas et al., "*In Vivo Real-Time Intravascular MRI*", Journal of Cardiovascular Magnetic Resonance, 4 (2), pp. 223–232, 2002 (the entire disclosure of which is hereby incorporated by reference), all of which suffer from the same or similar shortcomings mentioned above.

Therefore, there is a need in the art of medical imaging for an RF probe that provides high performance in both near field and the far field imaging. Further, there is a need in the art of medical imaging for an RF probe that avoids the incorporation of bulky external electrical components such as matching circuits and tuning circuits which not only adversely affect the size of its mechanical envelope but also add to the cost of the receiver.

SUMMARY OF THE INVENTION

Toward this end, the inventors herein have developed an RF probe for use with a medical imaging apparatus, the RF probe comprising an intracorporeal self-tuned resonator coil. The inventive coil provides excellent performance in both the near field and far field while having a minimal cross-sectional envelope. The inventive coil achieves a desired magnetic field distribution similar to that of a flat coil (thereby eliminating any significant near/far field transition zones) and a small profile similar to that of a loopless dipole design, all without the need for external tuning circuits or external matching circuits.

When the resonator coil is inserted into a patient's body and when RF pulses are applied to the body at a frequency substantially the same as the resonant frequency of the resonator coil, the resonator coil receives a signal responsive to the RF pulses that is representative of an image of an interior portion of the patient's body. The length of the resonator coil is an important factor affecting the resonator coil's resonant frequency. By appropriately setting its length, the resonator coil of the present invention can be tuned to substantially match the frequency of the RF pulses (such as the Larmour frequency of 63 MHz in a 1.5 T field).

Preferably, the resonator coil is coupled to a transmission medium that passes the signal from the resonator coil to a processor (the processor being configured to process the resonator coil signal to generate the image therefrom). The transmission medium has a characteristic impedance, and to prevent a standing wave from building up in the resonator coil, the resonator coil needs to be substantially self-matching with respect to the transmission medium's characteristic impedance.

Toward this end, a return lead of the transmission medium is coupled to an end of the resonator coil conductor. Further, a signal lead of the transmission medium is coupled to a selected point on the resonator coil winding, thereby defining a turns ratio for the resonator coil. By appropriately setting the resonator coil turns ratio, the resonator coil can be made to substantially self-match the transmission medium's characteristic impedance.

Because the resonator coil of the present invention allows for both self-tuning and self-matching, the bulky and relatively expensive tuning and matching circuits that are found in the prior art are unnecessary. As such, the cross-sectional envelope of the resonator coil of the present invention is greatly improved (minimized), which allows for the use of the present invention to image within hard to reach places, such as the interior of blood vessels.

Further, the resonator coil of the present invention is preferably an open coil. As such, and unlike the closed loop coil designs of the prior art, no heat will build up in the coil as RF energy is received. Because no heat is built up, the resonator coil of the present invention provides greater patient safety and comfort than prior art coil designs.

Further still, the present invention can be used to not only diagnose medical conditions such as tumors or arteriosclerosis, but it may also be used in connection with interventional treatments to monitor the delivery of substances such as therapeutic drugs, nanoparticles, genes, contrast agents, or the like into the patient's body. By monitoring the image derived from the resonator coil's received signal, a doctor can assess the substance's delivery into the patient's body and, if necessary, make adjustments to how the substance is delivered in response to the images.

Further, disclosed herein is a method of making the resonator coil of the present invention, the method comprising the steps of winding a conductor into an open resonator coil having a plurality of turns, the resonator coil having a pre-determined resonator length to provide a coil resonance substantially equal to a desired frequency. The method further comprising (1) selecting a coupling point at one end of the coil and a coupling point at an intermediate point on the coil, the selected coupling points defining a desired impedance for the coil that substantially matches the characteristic impedance of a transmission medium; (2) coupling a signal lead of a transmission medium to the selected intermediate coupling point; and (3) coupling a return lead of the transmission medium to the selected end coupling point, thereby rendering the coil substantially self-matching to the transmission medium's characteristic impedance.

These and other features and advantages of the present invention will be in part apparent and in part pointed out in the following description and referenced figures.

BRIEF DESCRIPTION OF THE DRAWINGS

FIG. 1 is an illustration of a prior art RF receiver using a single loop coil design;

FIGS. 2(a) and 2(b) are illustrations of a prior art RF receiver using a loopless antenna design;

FIG. 4(a) depicts the cross-sectional envelope of an unsheathed resonator coil;

FIG. 4(b) depicts the cross-sectional envelope of a sheathed resonator coil;

FIG. 9 is a Smith chart depicting measured impedance for another unloaded resonator coil;

FIGS. 19(a) and 19(b) depict the use of the resonator coil of the present invention to image an interior portion of a patient.

DETAILED DESCRIPTION OF THE PREFERRED EMBODIMENT

Figure 3A:
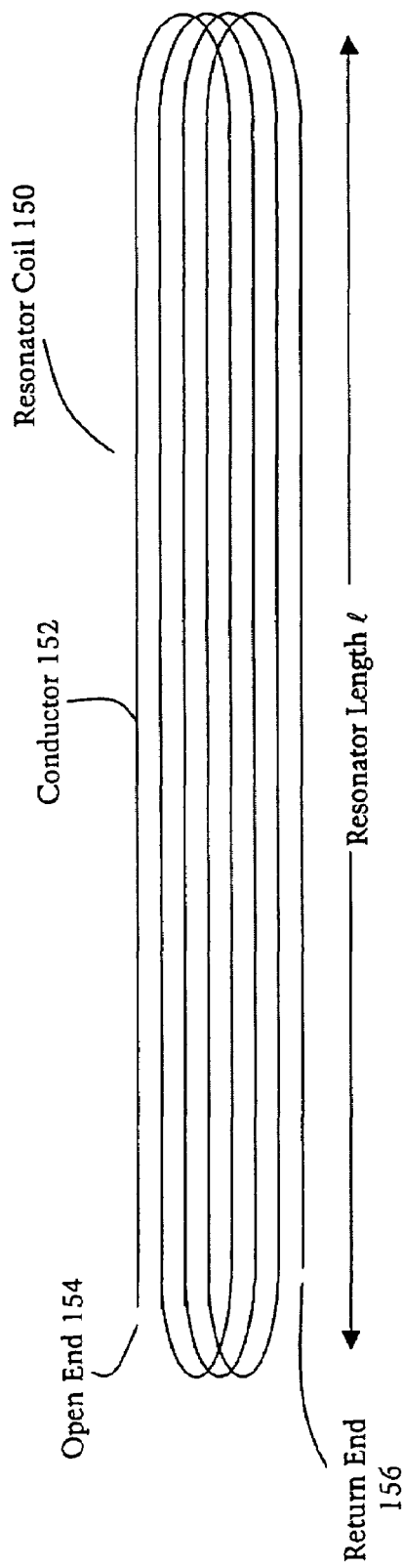
FIG. 3(a) depicts the resonator coil of the present invention.

FIG. 3(a) is depicts the resonator coil 150 of the present invention. Resonator coil 150 is made of a conductor 152 having an open end 154 and a return end 156. Conductor 152 is wound to create a plurality N of turns, thereby forming an open coil. As can be seen, the resonator coil 150 shown in FIG. 3(a) includes 4 turns. However, the actual number of turns that are used for the resonator coil is a design choice, and may be more or fewer than 4, as would be apparent to one of ordinary skill in the art following the teachings of the present invention.

Figure 3B:
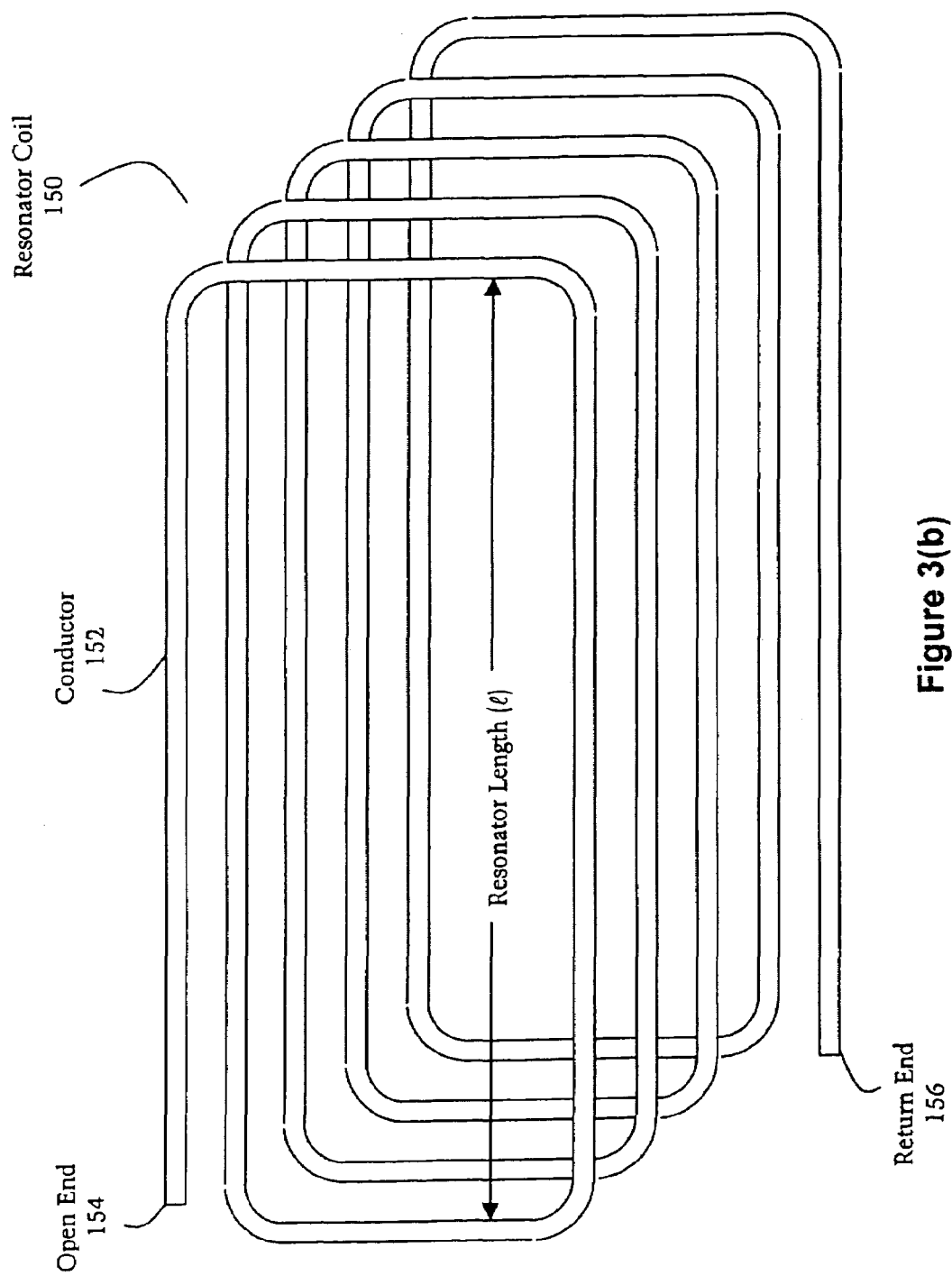
FIG. 3(b) is an exploded view of the resonator coil of the present invention.

The resonator coil 150 has a length l defined as the length between each turn as shown in FIGS. 3(a)–(d). As will be explained below, the resonator length l is an important factor affecting the resonant frequency of the coil, and the number of turns is an important factor affecting the ability of the coil to be self-matching with the characteristic impedance of a transmission medium connected thereto. FIG. 3(b) is an exploded view of the resonator coil 150, wherein the number of turns is 5.

Conductor 152 is preferably a flexible, small diameter wire such as 30 gauge copper wire or 36 gauge copper wire. However, other gauges of wire reasonably of a similar size may be used, as may non-magnetic wire materials other than copper, as would be apparent to one of ordinary skill in the art. To form the resonator coil 150, the conductor 152 may be hand wound. However, it is preferred that high accuracy industrial winding techniques be used to form a tight winding having a small cross-sectional envelope.

Figure 3C:
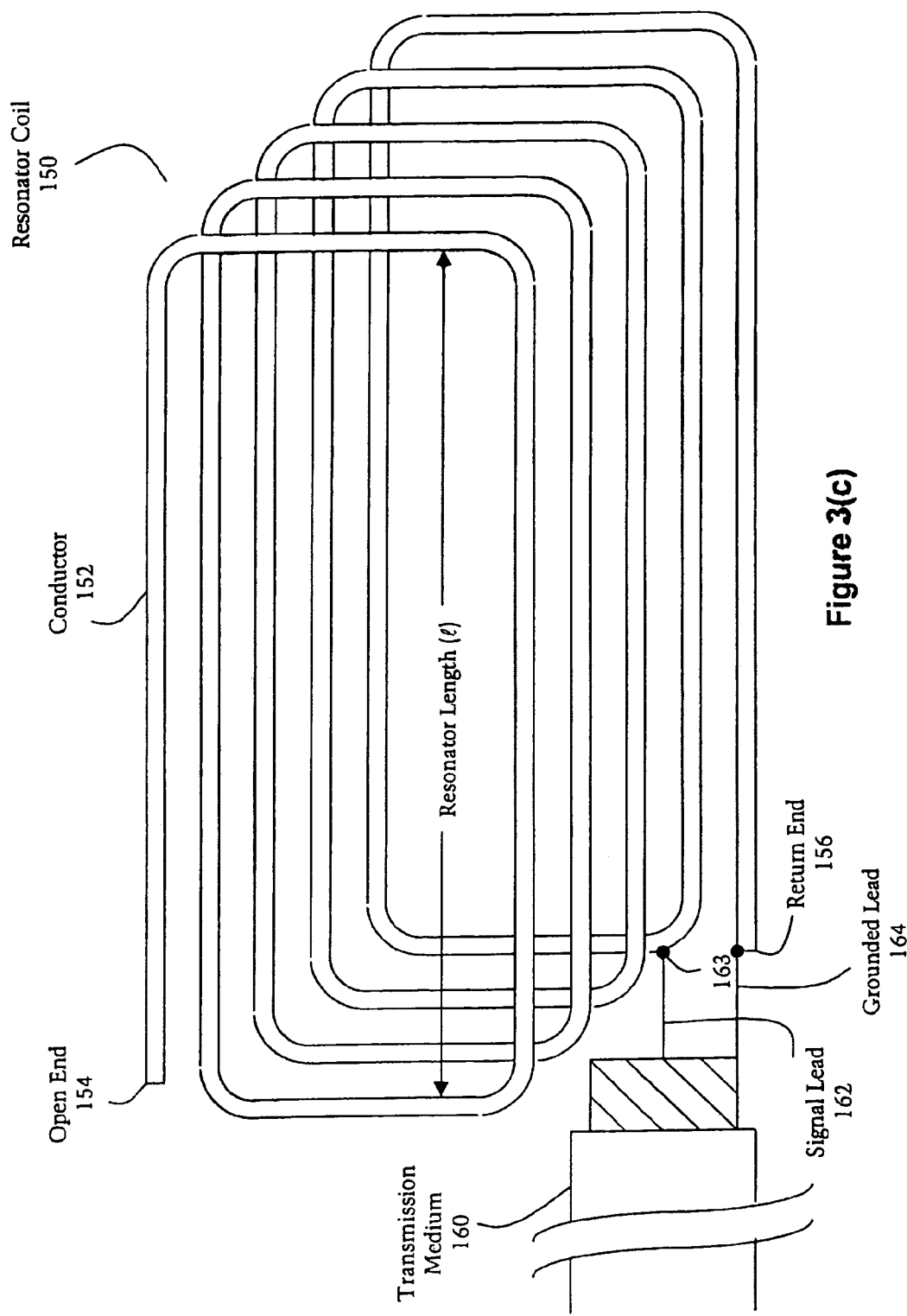
FIGS. 3(c) and 3(d) depict an exploded view of the resonator coil of the present invention coupled to a transmission medium such as a coaxial cable.
Figure 3D:
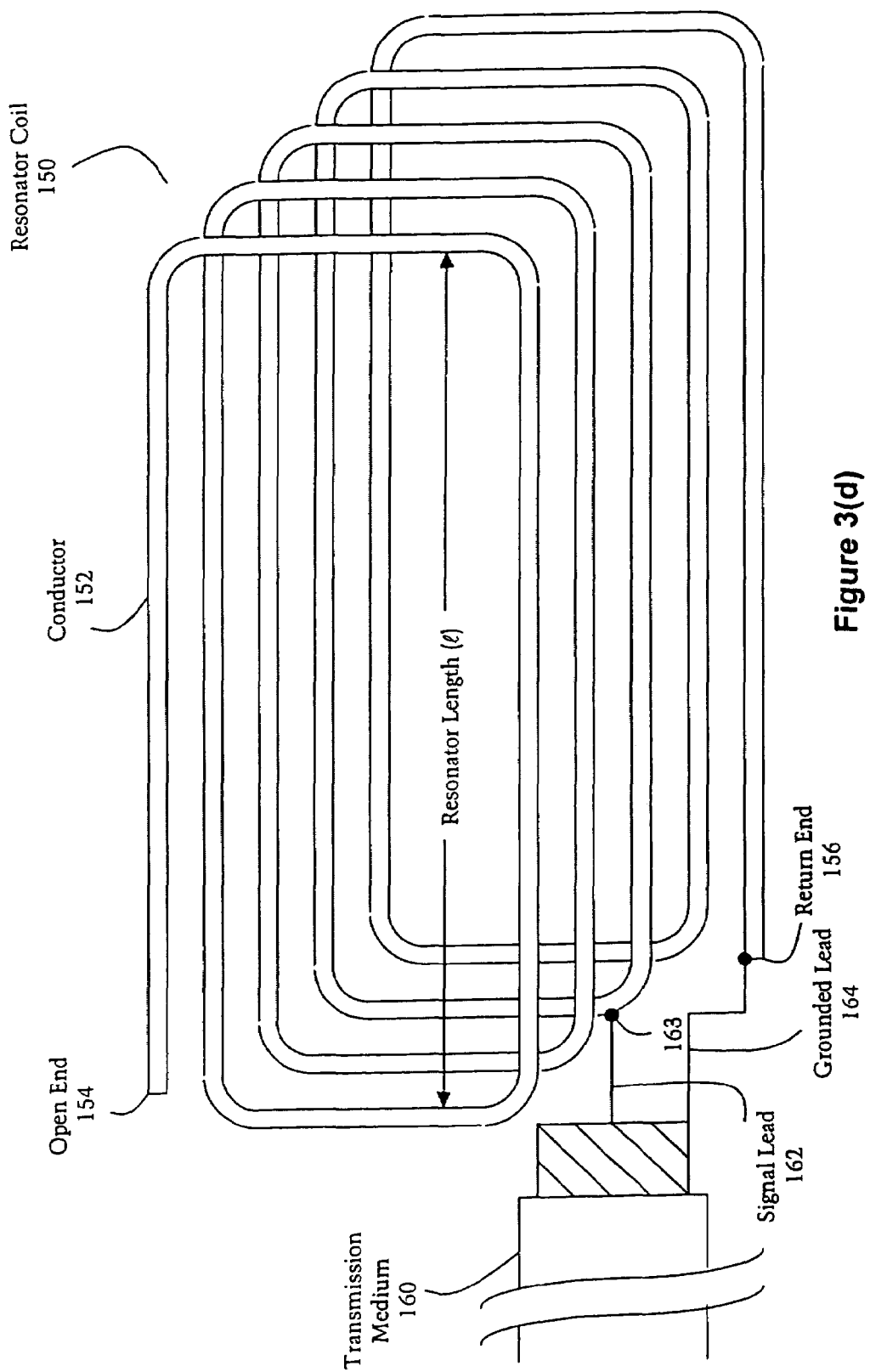

The resonator coil 150 is preferably connected to a transmission medium 160 as shown in FIGS. 3(c) and 3(d). Transmission medium 160 passes the signal sensed by the resonator coil 150 to an image processor (not shown). Transmission medium 160 is preferably a flexible small diameter coaxial cable. However, other types of transmission media may be used, such as a shielded twisted pair, as would be apparent to those of ordinary skill in the art.

Transmission medium 160 includes a signal lead 162 and a grounded lead 164. The grounded lead 164 is coupled to the return end 156 of the resonator coil 150. The signal lead 162 is coupled to any intermediate point along any of the turns of the resonator coil. The location 163 of coupling between the signal lead 162 and the resonator coil 150 defines a turns ratio for the resonator coil. The turns ratio is defined as the number of turns in primary winding (the resonator coil 150) to the number of turns in the secondary winding (the winding formed by the coupling of the transmission medium 160 to the resonator coil 150). The turns ratio is an important factor affecting the coil's self-matching capabilities, as will be explained below. Referring to FIG. 3(c), it can be seen that the turns ratio is 5:1, while in FIG. 3(d), the turns ratio is 5:2.

FIG. 4(a) shows the resonator coil (depicted representationally as block 150) coupled to transmission medium 160. The resonator coil 150 has a cross-sectional envelope 170. The diameter 172 ($d_{coil}$) of the cross-sectional envelope 170 can be sufficiently small to allow insertion of the resonator coil into very minute openings, such as blood vessels or other narrow lumens in the body. Even when the resonator coil 150 is disposed in an insulating sheath 180, as shown in FIG. 4(b), the cross-sectional envelope 182 for the sheathed resonator coil is very small. As such, the diameter 184 ($d_{sheath}$) is also sufficiently small for insertion of the sheathed resonator coil into minute openings, such as blood vessels or other narrow lumens. With hand wound implementations, the diameter 172 may be as small as 1.2 mm, and diameter 184 may be as small as 2.5 mm, depending upon the gauge of the wire used in the resonator coil 150, the number of turns in the resonator coil 150, and the material used as the sheath 180. Further, it is believed that through the use of manufacturer's microtechnology capabilities, much smaller diameters can be achieved. Given that wound wires used as guide wires with angioplasty balloons can have diameters as small as 0.36 mm, the inventors herein believe that the coil can be as small as 0.25 mm. A preferred range of diameters for the coil of the present invention is 1 mm to 2 mm.

Figure 5B:
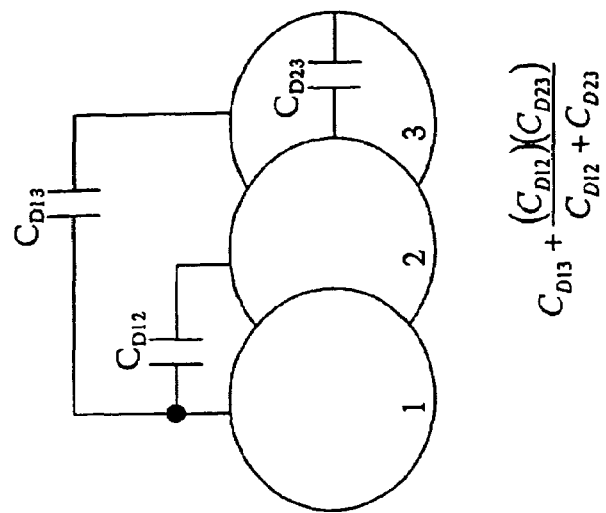
FIG. 5(b) depicts the distributed capacitance $C_D$.
Figure 5A:
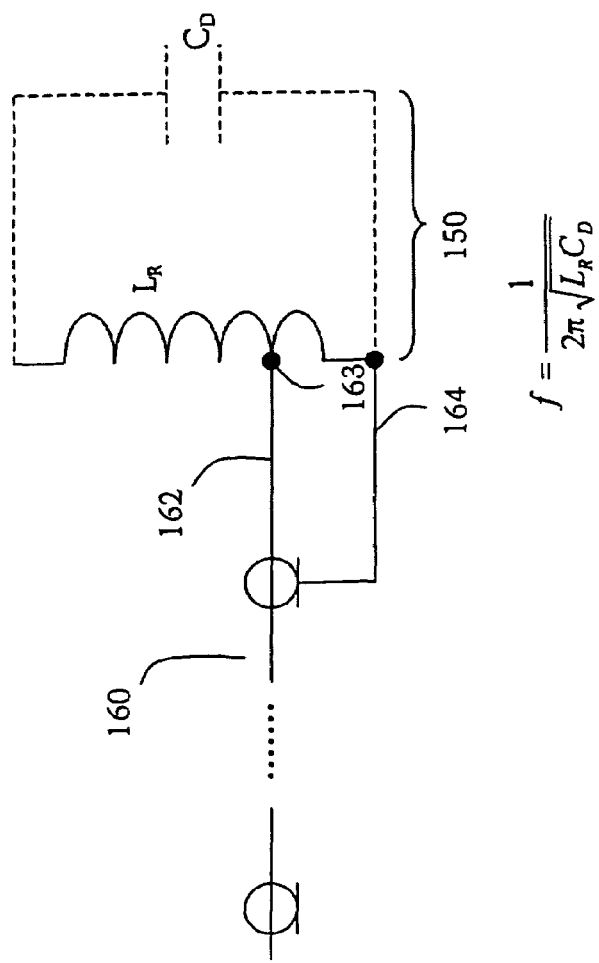
FIG. 5(a) is an equivalent circuit model for tuning the resonator coil of the present invention.

As previously mentioned, one of the advantages of the present invention is its capability to be self-tuned to a desired resonant frequency, thereby eliminating the need for external tuning circuits that are both bulky and relatively costly. FIG. 5(a) illustrates an equivalent circuit model for tuning the resonator coil. As is well-known, and with reference to the circuit of FIG. 5(a), the resonant frequency of a coil can be expressed by the formula:

$$f = \frac{1}{2\pi\sqrt{L_R C_D}}$$

wherein $L_R$ represents the inductance of the coil and $C_D$ represents the distributed (self) capacitance of the coil. See Roddy et al. "Electronic Communications", 1984, pp 34–35. $C_D$ depends upon the resonator's geometry. FIG. 5(b) illustrates how $C_D$ is affected when there are 3 coils of wire (coils 1–3). $C_D$ can be determined from the individual distributed capacitances shown in FIG. 5(b) as:

$$C_D = C_{D13} + \frac{(C_{D12})(C_{D23})}{C_{D12} + C_{D23}}$$

However, while aiding in the understanding of the invention, the formula above is not particularly helpful in tuning the resonator coil because of $C_D$'s high dependence on the resonator's geometry.

The most significant geometrical design factor in self-tuning the resonator coil 150 to a desired resonant frequency, as determined from empirical testing, is resonator length. While other resonator coil properties, such as wire diameter and turns ratio, also have an effect on the coil's resonance, those effects are insignificant. By appropriately selecting the resonator length, and then creating a winding having that length, a practitioner of the present invention can make the self-tuned resonator coil of the present invention.

Figure 6:
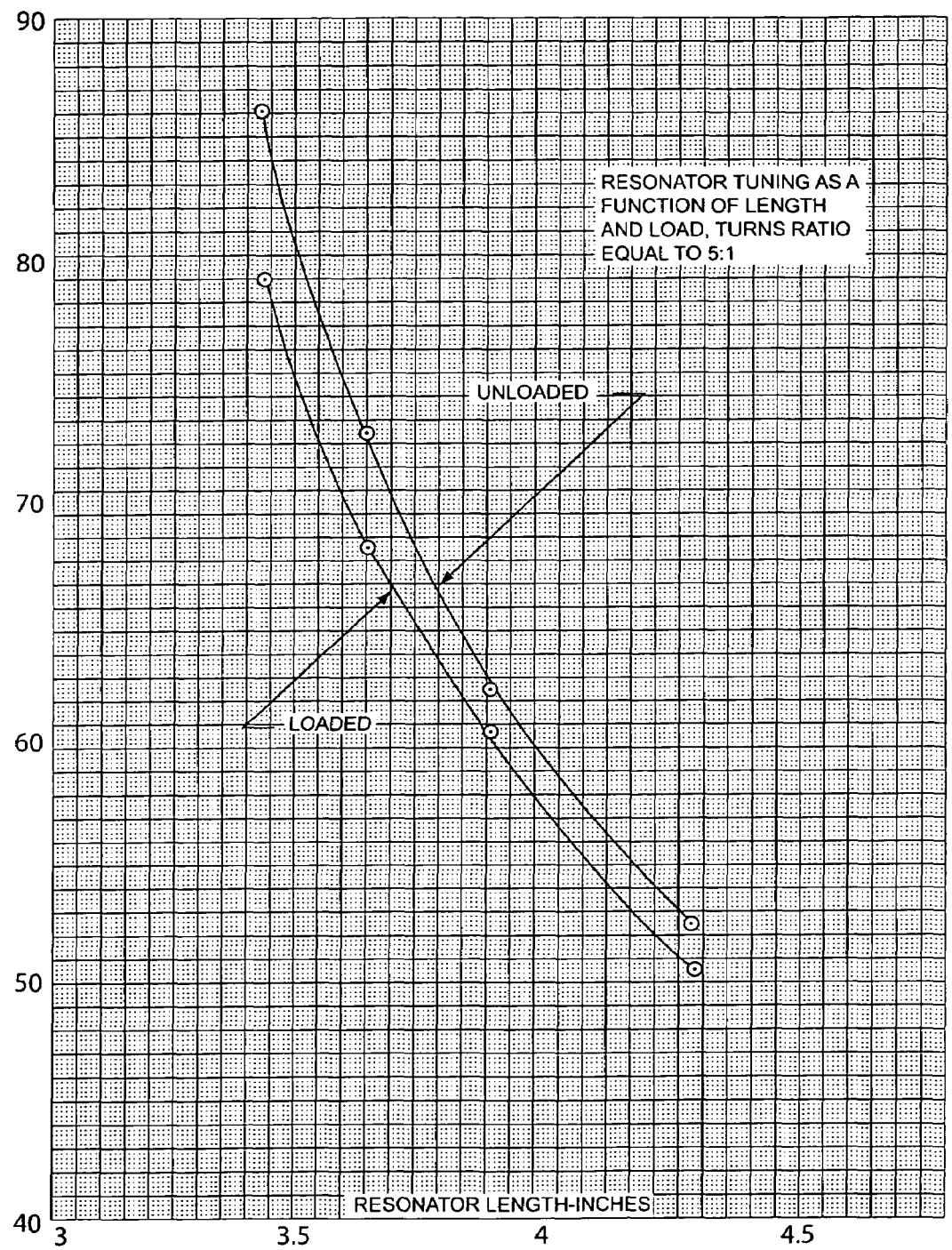
FIG. 6 is a graph illustrating resonant frequency as a function of resonator length.

FIG. 6 illustrates resonant frequency as a function of resonator length for a resonator coil formed from 32 gauge copper wire and having a turns ratio of 5:1. FIG. 6 shows plots for both an unloaded resonator coil and a loaded resonator coil. The resonator coil is considered "unloaded" when it is free standing in the air. While there is some dielectric loading from the surrounding air and the enamel paint on the wire, such loading causes negligible energy dissipation (the circuit's Q factor is high). The resonator coil is considered "loaded" once it is encased in an insulating sheath (see FIG. 4(b)), such as heat shrinkable tubing, and immersed in a dielectric. An insulating sheath increases the load on the resonator coil as energy is dissipated into the sheath. Similarly, when subjected to a dielectric (a conductive medium such as saline or the human body), the load on the resonator coil is further increased. The loading referenced in FIG. 6 was achieved by encasing the resonator coil in an insulating sheath and then immersing the sheathed resonator coil in a saline solution.

The data shown in FIG. 6 is reproduced below in Table 1.

TABLE 1

Tuning vs. Resonator Length

| Resonator Length (in) | Resonant Frequency- Loaded (MHz) | Resonant Frequency- Unloaded (MHz) | % Frequency Change (Unloaded to Loaded) |
|---|---|---|---|
| 3.5 | 79.4 | 86.6 | −8.31% |
| 3.65 | 68.2 | 73 | −6.58% |
| 3.9 | 60.2 | 62 | −2.90% |
| 4.3 | 50 | 52 | −3.85% |

A slight curvature exists in this tuning curve. While a linear relationship is expected, the curvature shown in FIG. 6 may be due to variations in the fabrication of different resonator coils used in the experiment, which were hand wound. If a higher quality manufacturing process is used to produce the resonator coil of the present invention, a more linear tuning curve is expected.

Matching the resonator coil with the characteristic impedance of the transmission medium is primarily a function of resonator length and turns ratio. Because it is preferred that the length of the resonator coil be used to self-tune the resonator coil to a desired frequency, it is also preferred that the turns ratio be used as the variable to self-match the resonator coil with the characteristic impedance of the transmission medium.

Figure 7:
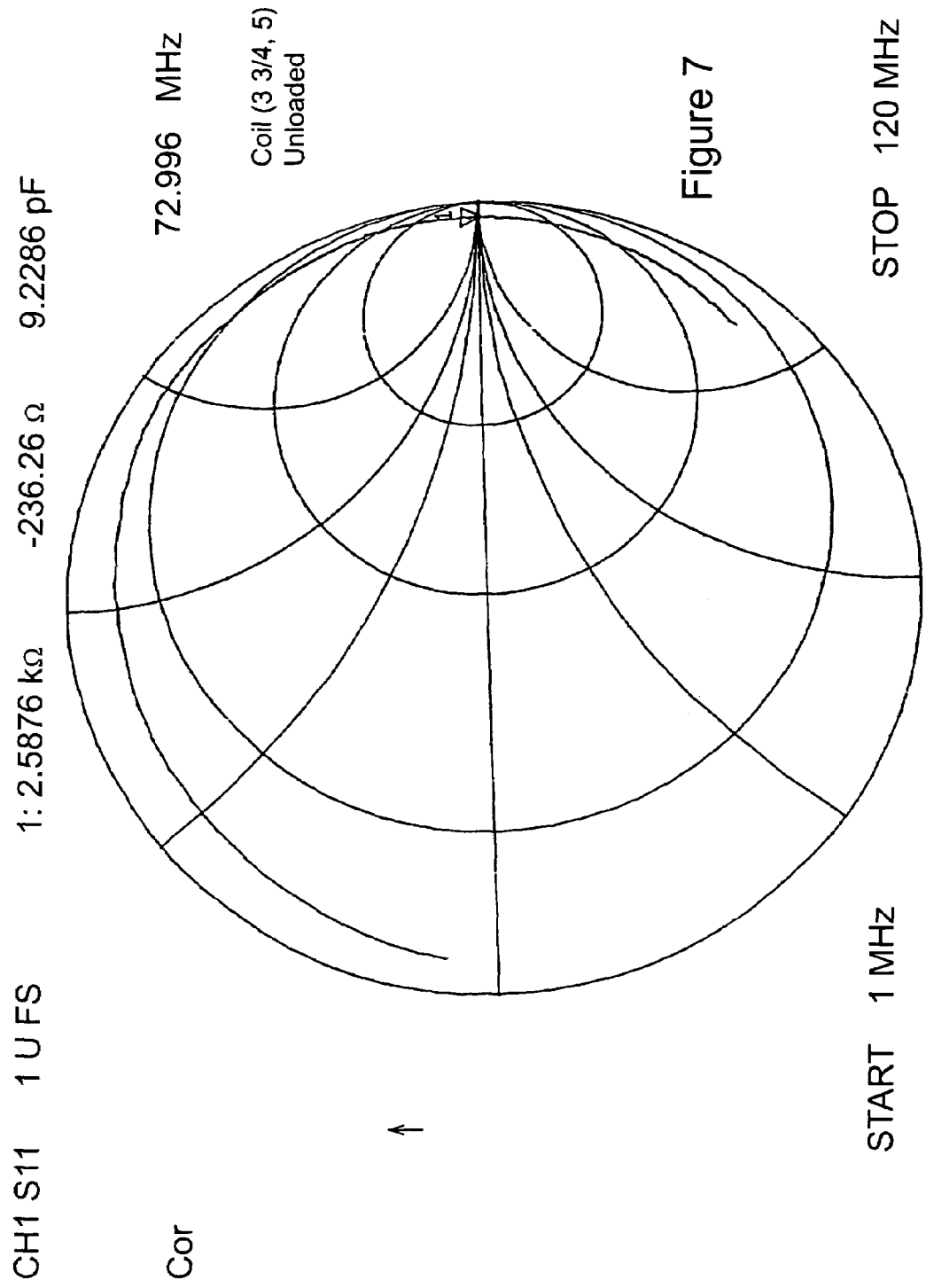
FIG. 7 is a Smith chart depicting measured impedance for an unloaded resonator coil.

The characteristic load of the resonator coil can be estimated by measuring the reflected impedance of the resonator coil with a network analyzer (for both the loaded and unloaded states). FIG. 7 is a Smith chart illustrating the reflected impedance for an unloaded resonator coil formed from 32 gauge copper wire, having a length of 3¾ inches, a 5:1 turns ratio, and a resonant frequency of around 73 MHz. From this figure, it can be seen that the real portion of the coil's load is around 2600 Ω at a low capacitance value of around 9 pF, which is indicative of parallel or high impedance resonance.

Figure 8:
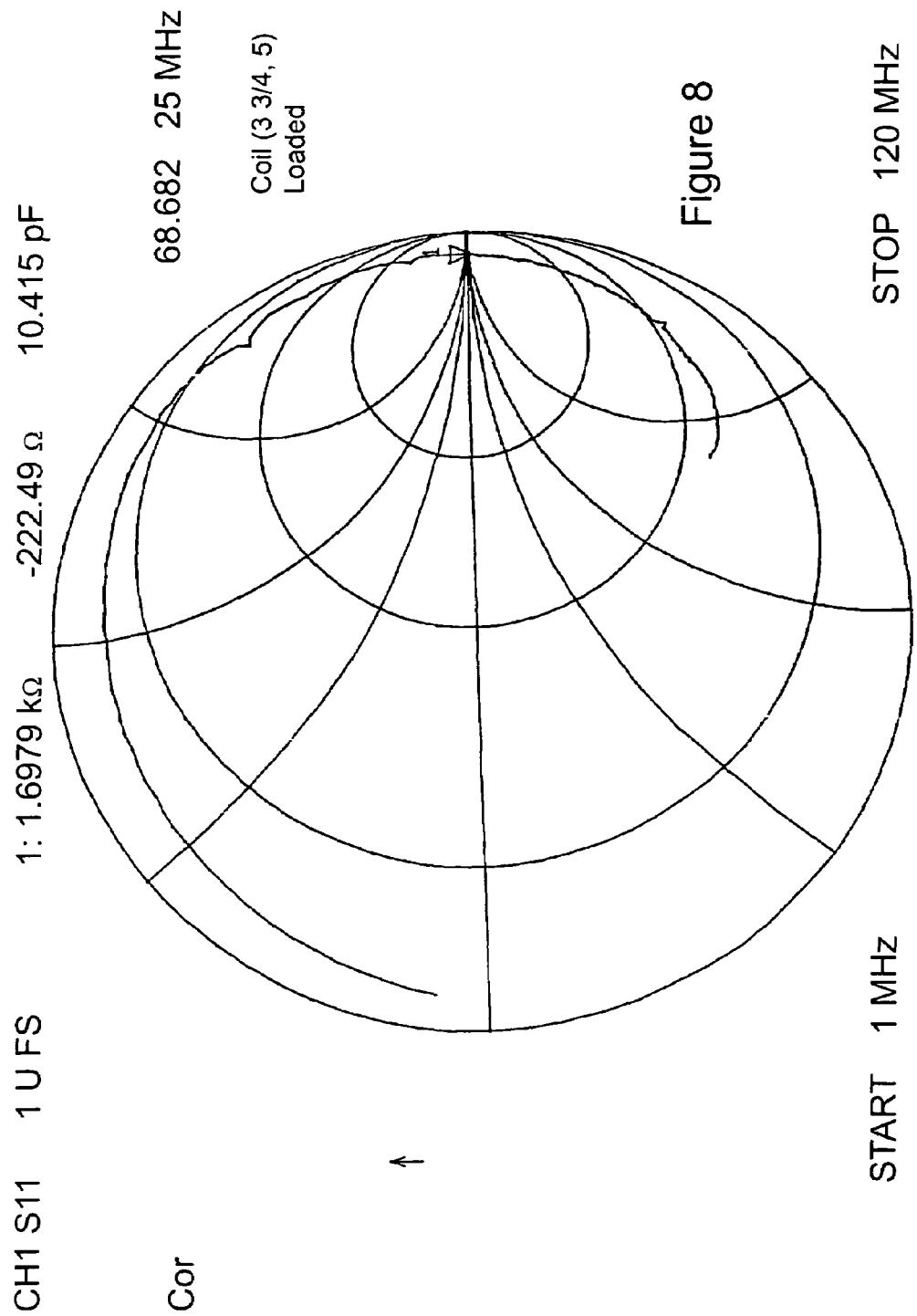
FIG. 8 is a Smith chart depicting measured impedance for a loaded resonator coil.

FIG. 8 is a Smith chart illustrating the reflected impedance for a loaded resonator coil (sheathed and immersed in saline) formed from 32 gauge copper wire, having a length of 3¾ inches, and a 5:1 turns ratio, and a resonant frequency of around 68.7 MHz. From this figure, it can be seen that the real portion of the coil's load has decreased to around 1700 Ω.

FIG. 9 is a Smith chart illustrating the reflected impedance for an unloaded resonator coil formed from 36 gauge copper wire, having a length of 3⅞ inches, a 5:1 turns ratio, and a resonant frequency of around 67.1 MHz. From this figure, it can be seen that the real portion of the coil's load is around 3150 Ω.

Figure 10A:
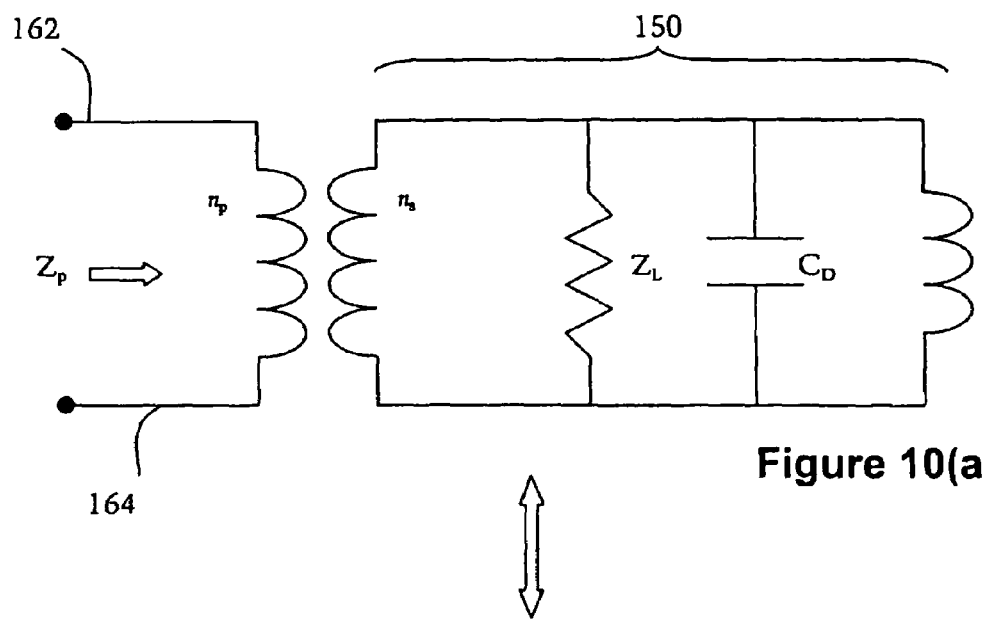
FIGS. 10(a) and 10(b) depict approximate impedance matching circuit models for the resonator coil.
Figure 10B:
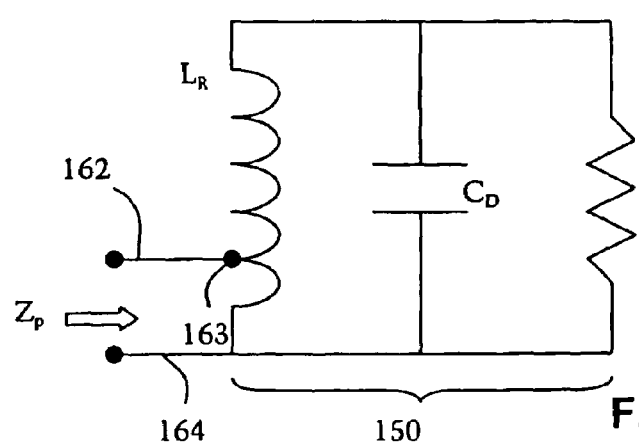

For a resonator coil having a given length, matching can be achieved through the use of a proper turns ratio. Referring to FIGS. 10(a) and 10(b) which depict an approximate impedance matching circuit model for the resonator coil, the impedance is reflected through the coil (transformer) as the square of the turns ratio. Thus, for a 5:1 turns ratio, the impedance matching ratio is $(5:1)^2$ or 25:1. In the case of the loaded resonator coil used in connection with FIG. 8, the value for $Z_p$ is $(1700\ \Omega)/(5^2)$ which equals approximately 67 Ω; 67 Ω being a reasonably good match to the 50 Ω characteristic impedance of the transmission medium. To ensure that no significant transmission loss occurs and that no unwanted radiation is present due to mismatching, the voltage standing wave ratio (VSWR) between the resonator coil and the transmission medium should be no greater than 2:1. However, as would be understood by those of ordinary skill in the art, the design parameters for the resonator coil (resonator length and turns ratio) can be optimized through empirical testing to arrive at a desirably high degree of impedance matching.

While turns ratio has a significant impact on resonator coil matching, the turns ratio does not have a significant effect on resonator coil tuning. This fact can be explained because the high impedance matching of the present invention provides a high parallel real part (resistance) of the impedance, which does not degrade the resonator coil's Q. For example, for the unloaded and loaded real impedance values of 2700 Ω and 1700 Ω respectively, the resonator coil's Q changes from 90 to 57. For a significant impact on resonator coil tuning, the resonator coil's Q would have to fall to 10 or less.

Because turns ratio has an impact on matching, but not tuning (while resonator length has an impact on both tasks), it is relatively easy to both self-tune and self-match the resonator coil of the present invention by first finding a resonator length that tunes the resonator coil to a desired resonant frequency, and then setting the turns ratio such that the resonator coil substantially matches the characteristic impedance of the transmission medium. To tune a loaded resonator coil to the Larmour frequency (the gyromagnetic ratio of the species to be imaged multiplied by the field strength, which for protons at 1.5 T is around 63 MHz) and match the resonator coil to a 50 Ω transmission medium, a practitioner of the present invention can set the resonator length equal to around 4⅛ inches and the turns ratio equal to 5:1 (see FIG. 13).

Figure 11:
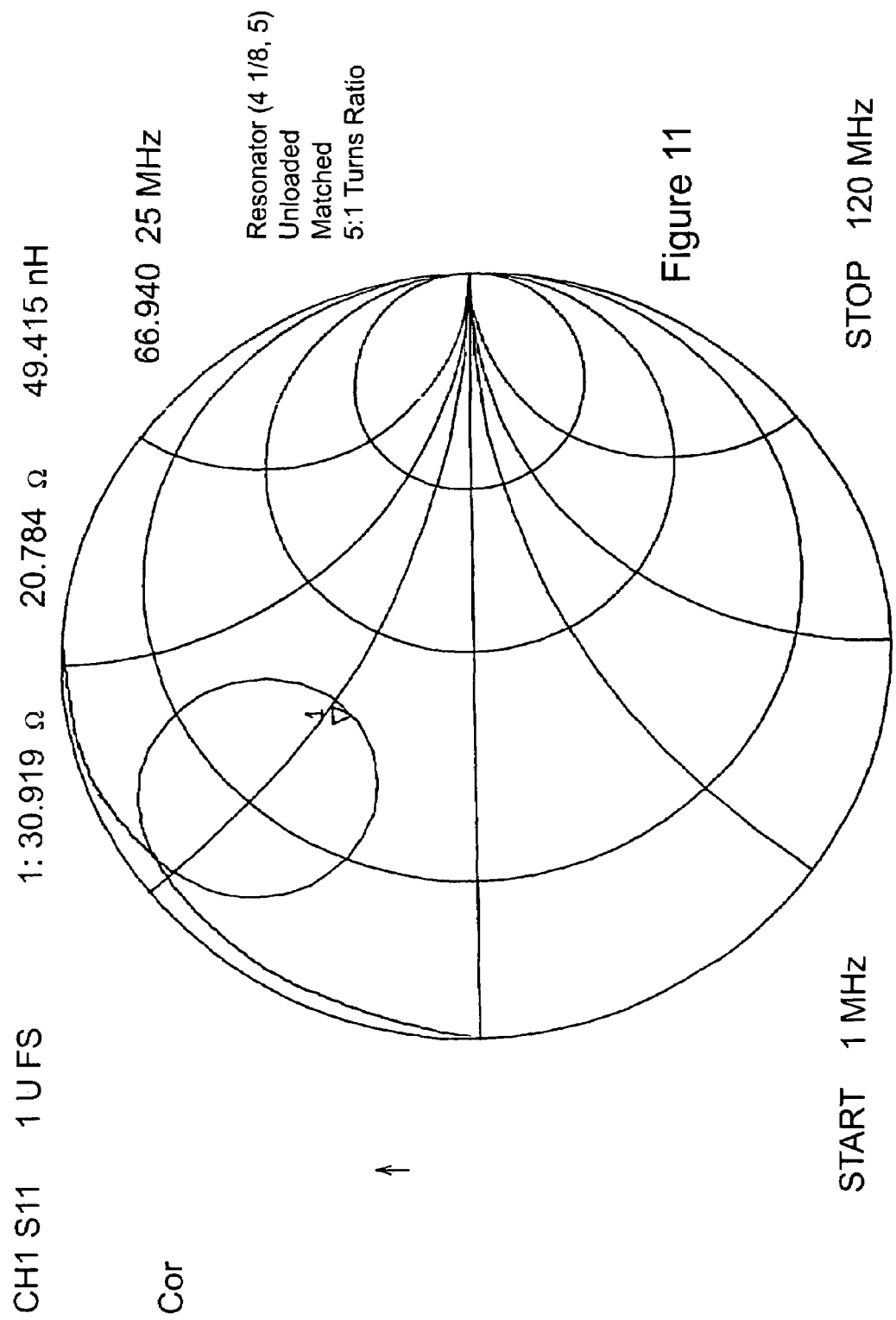
FIG. 11 is a Smith chart depicting the measured matched impedance for an unloaded resonator coil.
Figure 12:
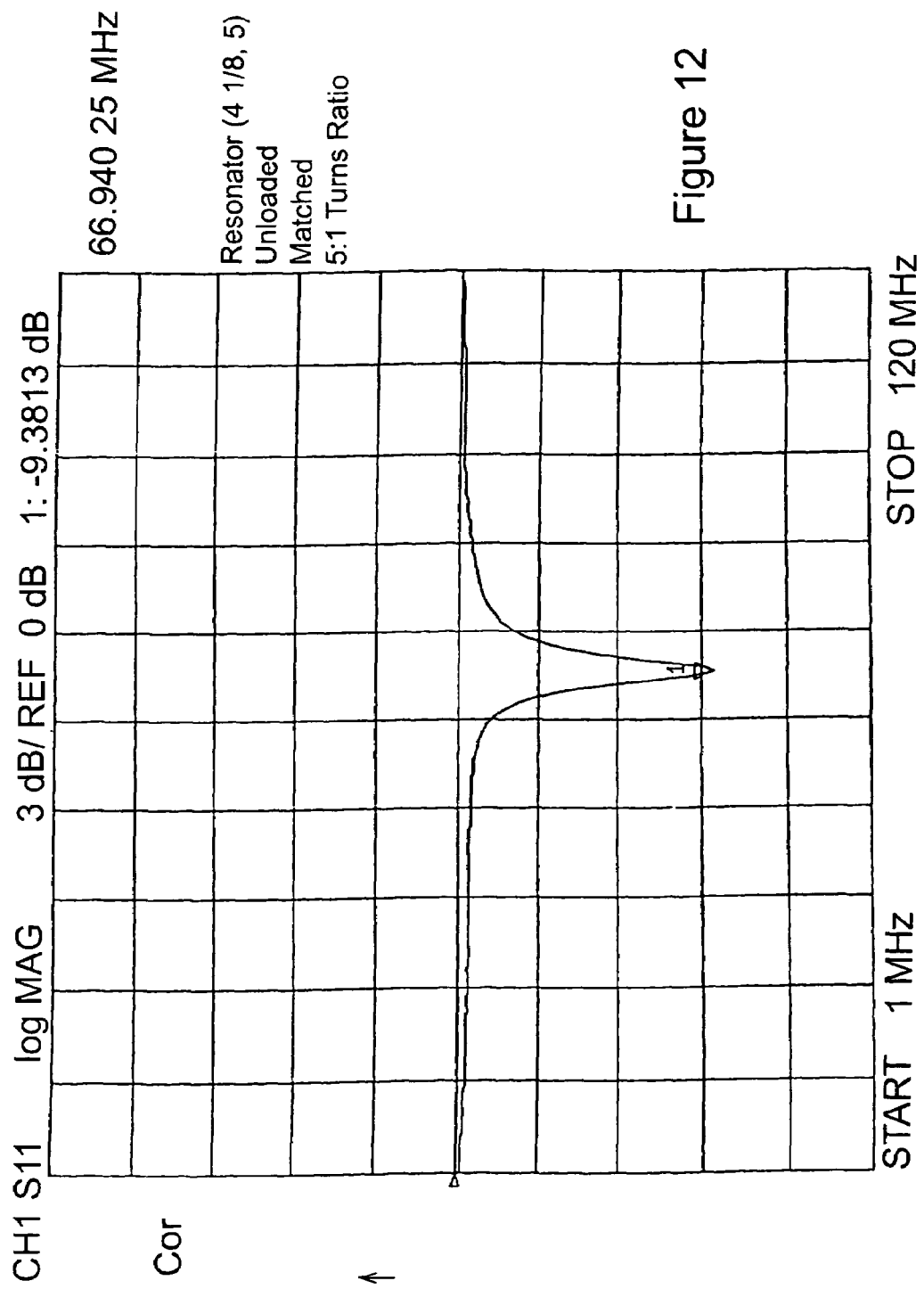
FIG. 12 is a graph depicting the return loss for the resonator coil of FIG. 11.

FIG. 11 is a Smith chart depicting a measurement of the matched impedance for an unloaded resonator coil formed from 32 gauge copper wire, having a length of 4⅛ inches, a 5:1 turns ratio, and a resonant frequency of about 67 MHz. FIG. 12 illustrates the return loss for such a resonator coil. As can be seen, the return loss is about 9.4 dB.

Figure 13:
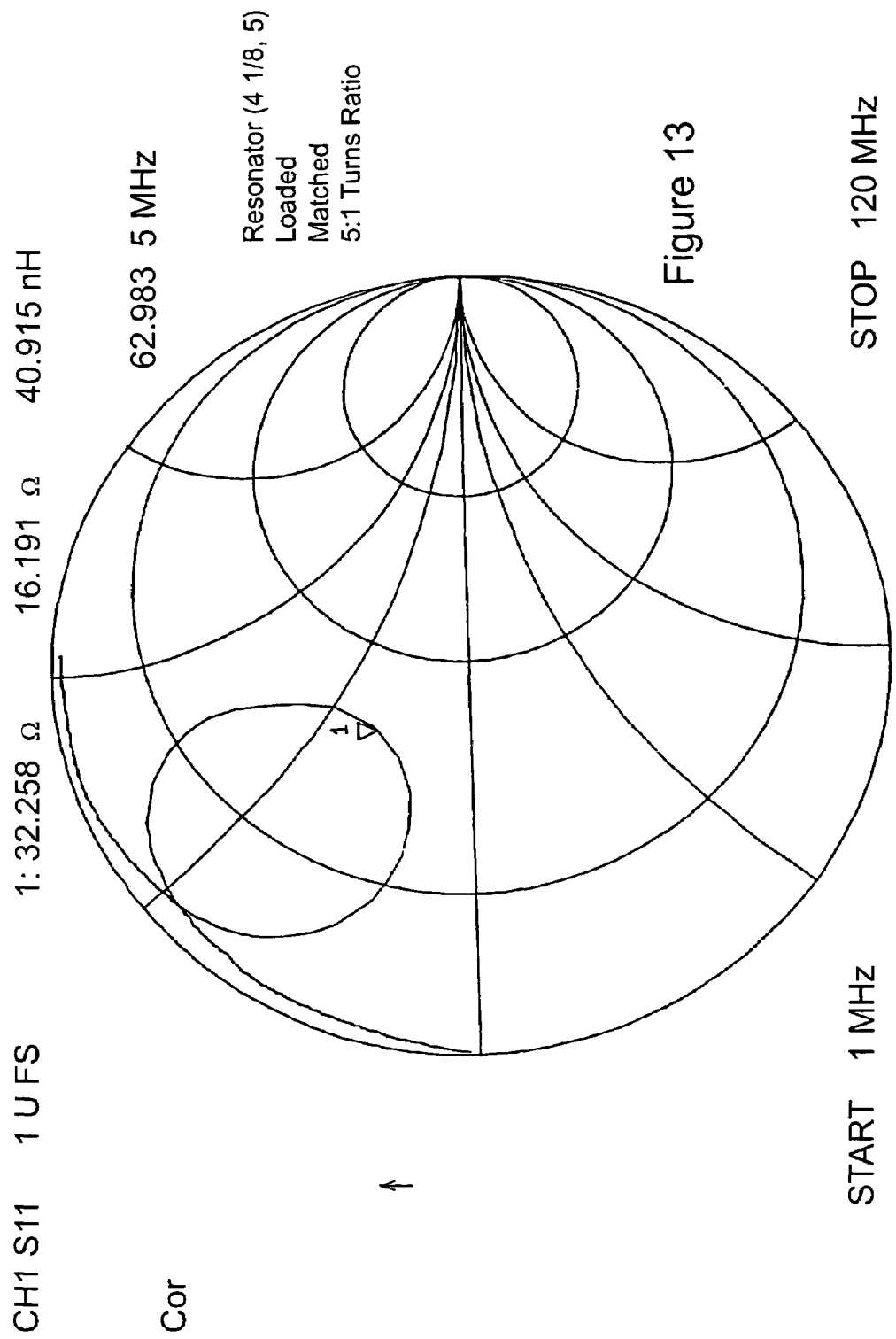
FIG. 13 is a Smith chart depicting the measured matched impedance for a loaded resonator coil.
Figure 14:
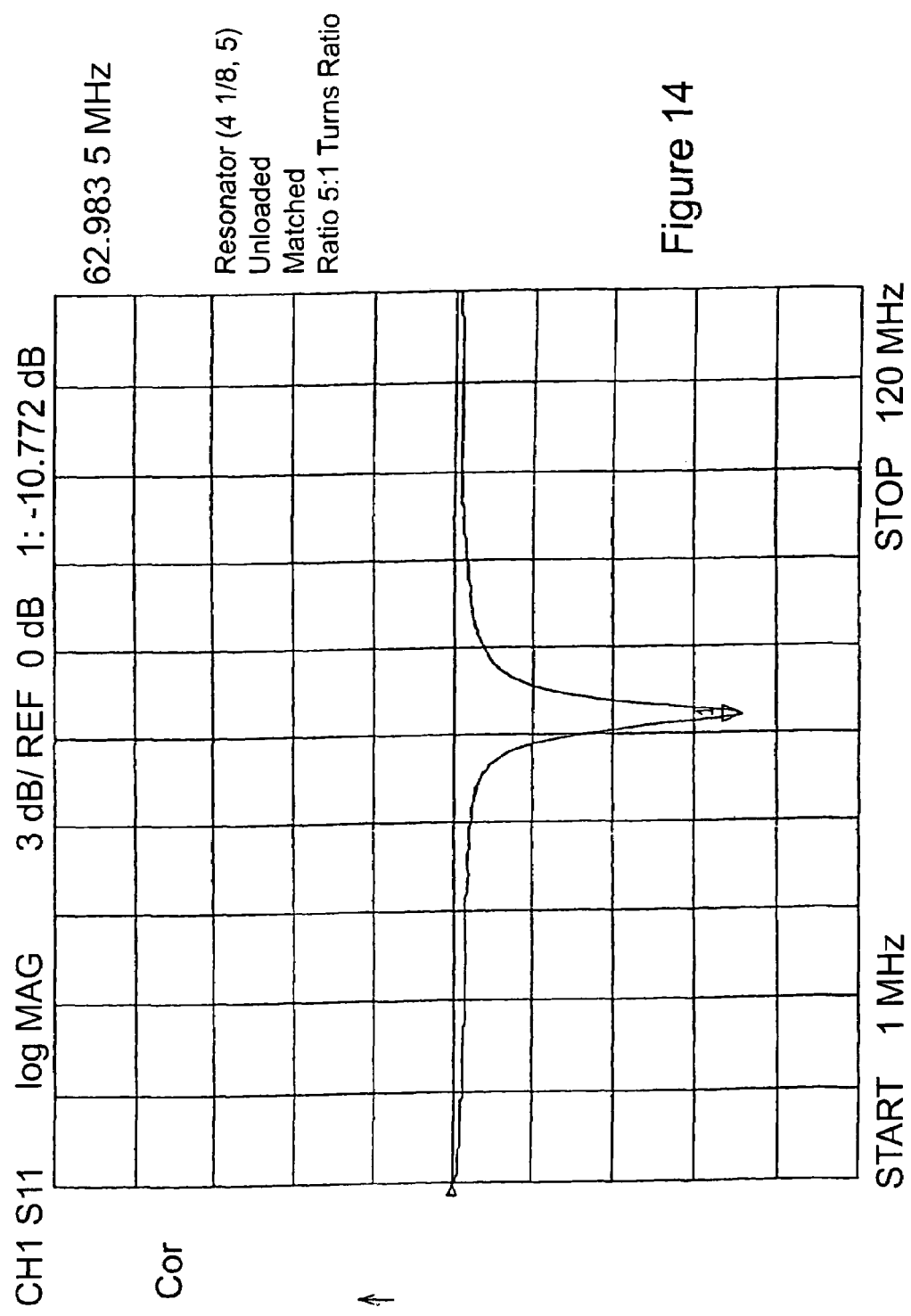
FIG. 14 is a graph depicting the return loss for the resonator coil of FIG. 13.

FIG. 13 is a Smith chart depicting a measurement of the matched impedance for a loaded resonator coil (sheathed and immersed in saline) formed from 32 gauge copper wire, having a length of 4⅛ inches, a 5:1 turns ratio, and a resonant frequency of about 63 MHz. FIG. 14 illustrates the return loss for such a resonator coil. As can be seen, the return loss is about 10.8 dB.

Figure 15:
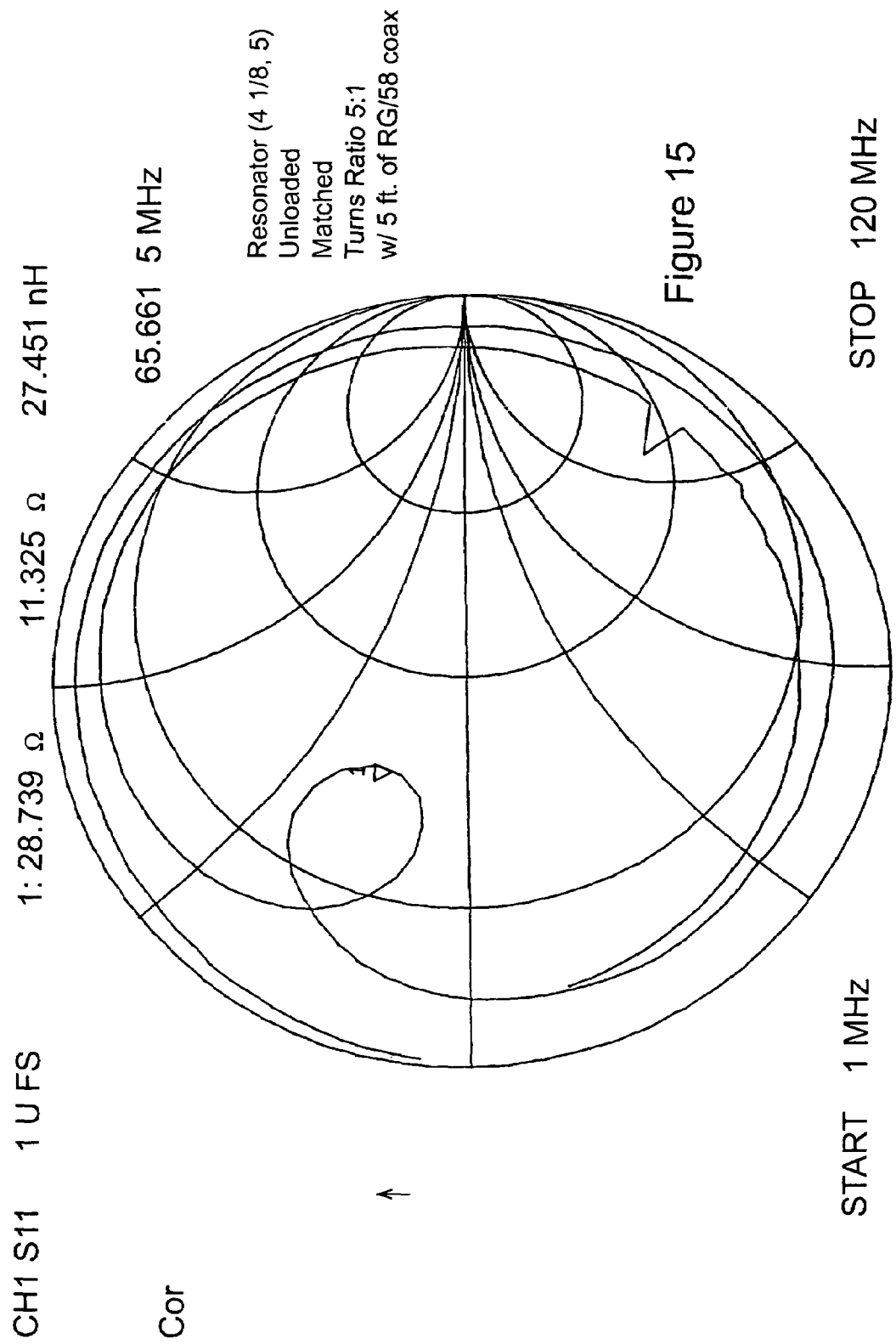
FIG. 15 a Smith chart depicting the measured matched impedance for the unloaded resonator coil of FIG. 11, wherein a 5 ft coaxial cable is coupled to the resonator coil.
Figure 16:
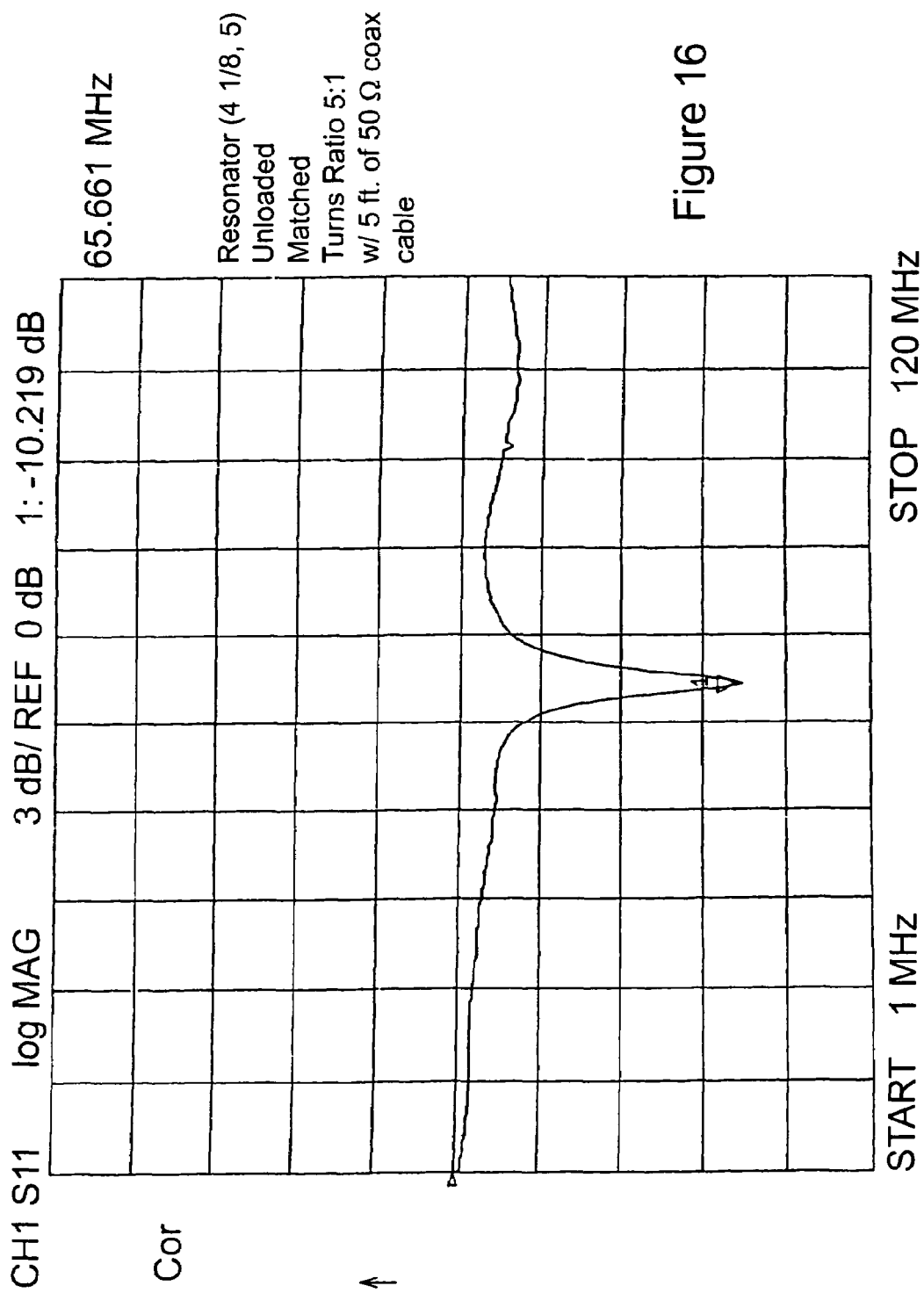
FIG. 16 is a graph depicting the return loss for the resonator coil of FIG. 15.

FIGS. 15 and 16 repeat the matched impedance measurement and return loss measurement performed with the unloaded resonator coil of FIGS. 11 and 12, with the exception being that a 5 foot length of RG/58 coaxial cable is coupled to the resonator coil. As can be seen from FIG. 16, the return loss is about 10.2 dB.

Figure 17:
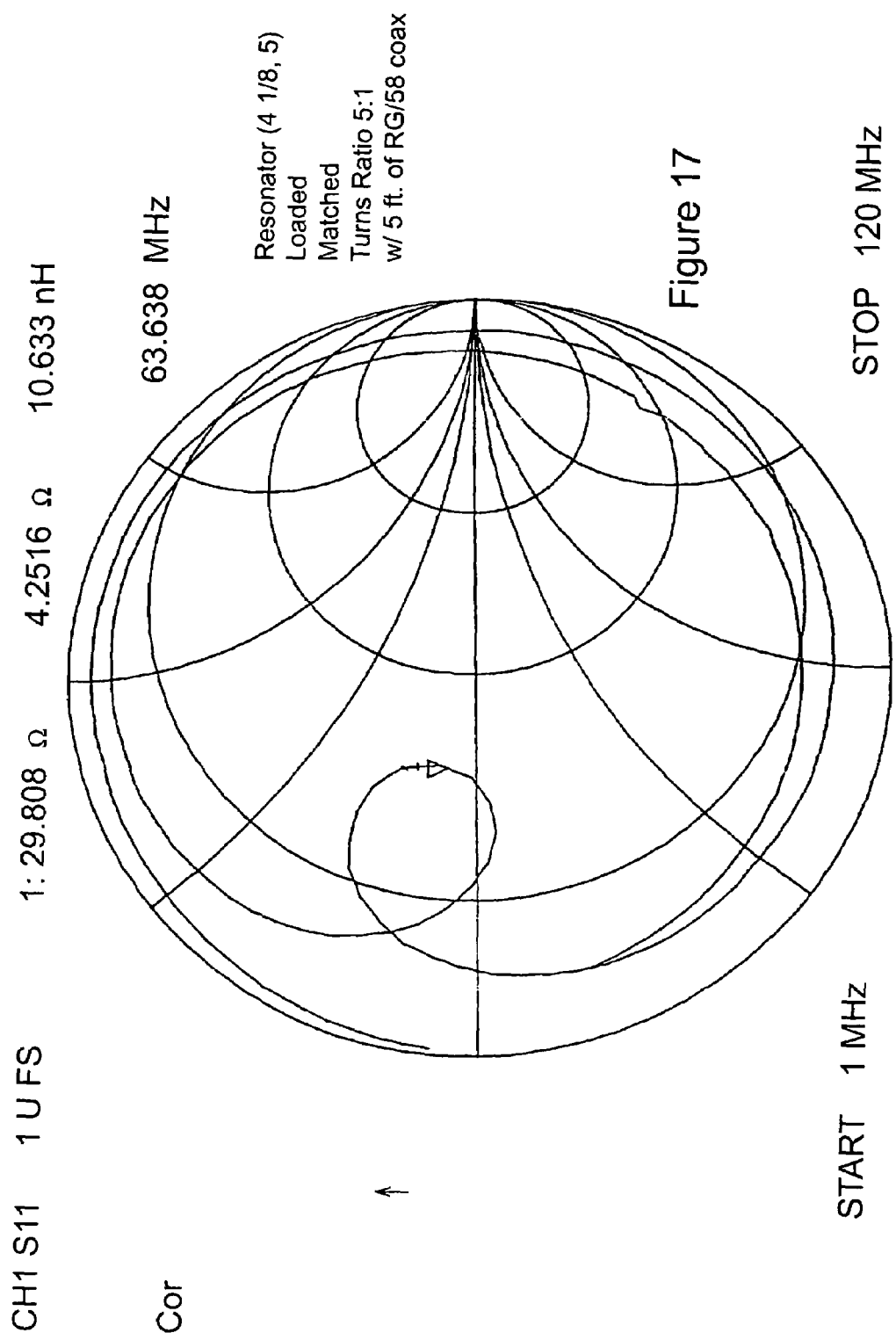
FIG. 17 a Smith chart depicting the measured matched impedance for the loaded resonator coil of FIG. 13, wherein a 5 ft coaxial cable is coupled to the resonator coil.
Figure 18:
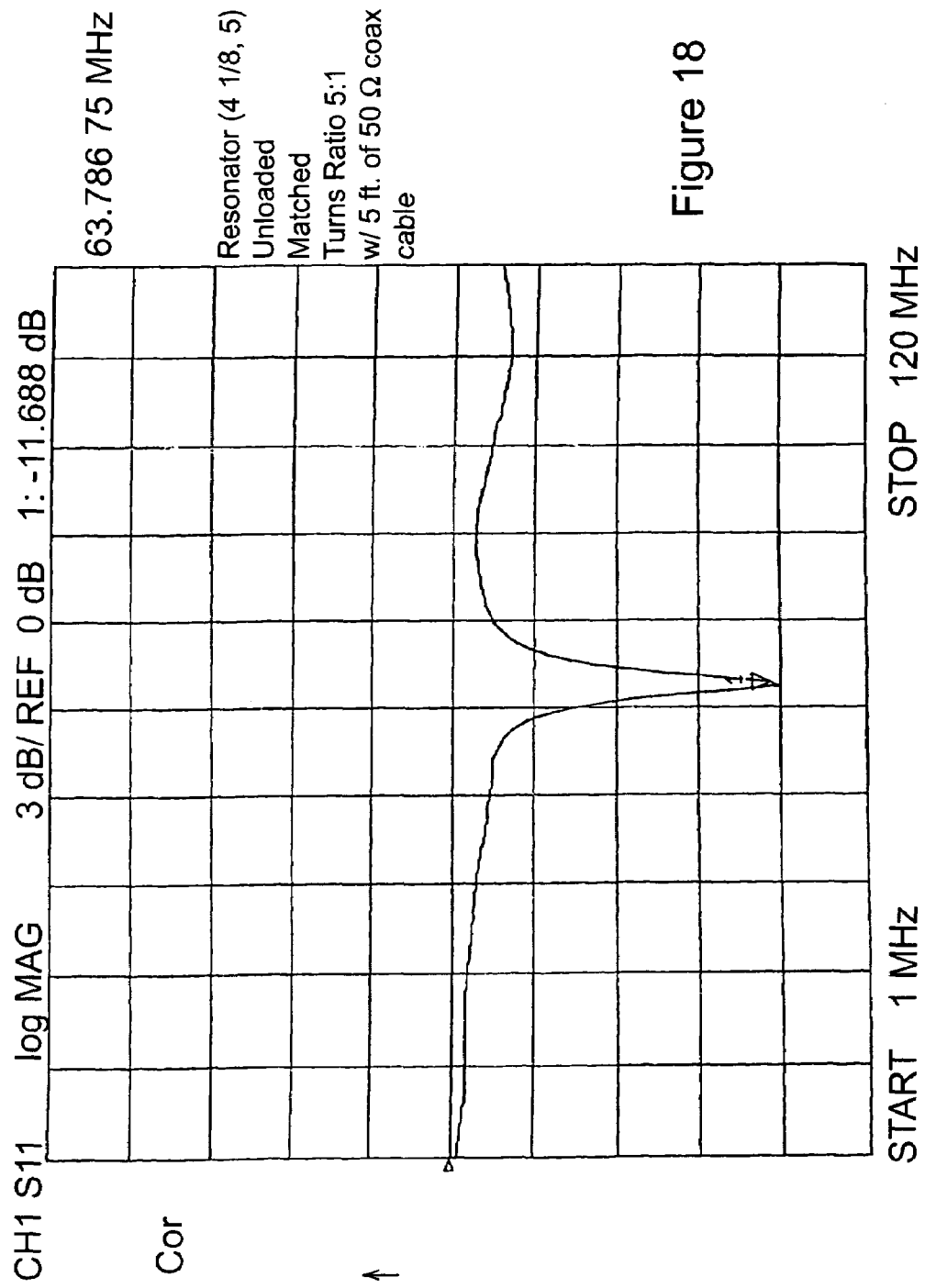
FIG. 18 is a graph depicting the return loss for the resonator coil of FIG. 17.

FIGS. 17 and 18 repeat the matched impedance measurement and return loss measurement performed with the loaded resonator coil of FIGS. 13 and 14, with the exception being that a 5 foot length of RG/58 coaxial cable is coupled to the resonator coil. As can be seen from FIG. 18, the return loss is about 11.7 dB.

FIGS. 13–18 show that the resonator coil is well-behaved when loaded and also suitably matched to the 50 Ω transmission medium, maintaining at least a 10 dB loss for both short and long coaxial cable configurations.

FIGS. 19(*a*) and 19(*b*) illustrate how the present invention can be used to image an interior portion of a patient's anatomy. The scope of imaging modalities supported by the coil of the present invention encompasses all MRI visible species, including fluorine sodium, potassium, phosphorus, manganese, carbon, etc., as would be appreciated by those of ordinary skill in the art following the teachings herein. Further, in addition to imaging analysis, the present invention may also be used for spectroscopy analysis.

The medical imaging apparatus 195 shown in FIGS. 19(*a*) and 19(*b*) includes the resonator coil and transmission medium (which are disposed in the imaging catheter 192) and an image processor 194. The resonator coil is in communication with the image processor 194 via the transmission medium coupled therebetween. Although the resonator coil is disposed within the imaging catheter 192 in FIGS. 19(*a*) and (*b*), this need not be the case as the coil may be used in conjunction with other insertion techniques, as would be readily understood by those of ordinary skill in the art.

Imaging catheter 192 is inserted into the body of patient 190 at insertion point 196. When RF pulses are delivered to the patient's body, the resonator coil will begin receiving a signal that can be translated by the image processor 194 to produce a medical image, such as an MR image, of the interior portion of the patient's body within field of view 198. Due to the resonator coil's small cross-sectional envelope, the resonator coil of the present invention is sufficiently small for insertion into very small openings, such as the coronary artery or a 3 mm artery. As such, the present invention is highly suitable for intravascular imaging to diagnose conditions such as arteriosclerosis (including atherosclerosis), brain imaging to diagnose brain tumors, and MR arthroscopy. The resonator coil of the present invention is also highly suitable for such diagnostic tasks as generating images of the bladder, liver (through insertion into the hepatic vein or artery), pancreas, prostate (through insertion via the urethra), stomach, esophagus, colon, spine, trachea, bronchi, etc.; such images being helpful to determine whether any pathology is present. Further, the coil is also useful for minimally invasive surgery, MR guidance (including the use of passive or active visible elements affixed to the coil containing catheter), interventional MR, and the guidance of surgical instruments.

Further still, as shown in FIG. 19(*b*), the resonator coil of the present invention can be used as an adjunct to the delivery of substances such as therapeutic drugs, nanoparticles, polymers (including dendrimers), contrast agents, mixtures of materials with contrast agents, genes, paramagnetic materials, superparamagnetic materials, ferromagnetic materials, viruses, and the like into the patient's body. As such substances are delivered to the body, either through a separate delivery device 200 as shown in FIG. 19(*b*) (which may be any medical device for injecting a substance into the body—needles, catheters, etc.) or through a channel in the catheter 192, the resonator coil of the present invention can provide real-time feedback as to the accuracy of the substance's delivery. As a substance is delivered to the patient's body within the field of view 198 of the resonator coil, the resonator coil receives a signal representative of that portion of the patient's inner anatomy and passes that received signal to the image processor 194. Once the image processor 194 generates a meaningful image from the resonator coil's signal and that image is displayed, a doctor can make an assessment as to whether his/her delivery of the therapeutic substance is accurate. Depending on the outcome of that decision, the doctor can change the location of substance delivery to thereby improve the patient's treatment.

Yet another application for the coil of the present invention is in connection with image-guided angioplasty, wherein an angioplasty balloon is attached around the coil and inserted into a vessel. Further, drug delivery can be achieved through the balloon. If the balloon is porous, nanoparticles (or other paramagnetic agents) could be injected through the balloon as the balloon is expanded within the vessel. In such cases, the coil could be used simultaneously to visualize the delivery of nanoparticles (or other paramagnetic agents) through the balloon into the vessel or tissue.

While the present invention has been described above in relation to its preferred embodiment, various modifications may be made thereto that still fall within the invention's scope, as would be recognized by those of ordinary skill in the art. Such modifications to the invention will be recognizable upon review of the teachings herein. As such, the full scope of the present invention is to be defined solely by the appended claims and their legal equivalents.

What is claimed is:

1. An RF probe for use with a medical imaging apparatus, said RF probe comprising an intracorporeal self-tuned resonator coil and wherein the resonator coil is self-tuned to a frequency of substantially the Larmour frequency.

2. The probe of claim 1 wherein the resonator coil is an open coil.

3. The probe of claim 2 wherein the resonator coil is adapted for coupling with a transmission medium for passing a signal from the resonator coil to a processor, the transmission medium having a characteristic impedance, and wherein the resonator coil is substantially self-matching with the transmission medium's characteristic impedance.

4. The probe of claim 3 wherein the resonator coil comprises an open wound conductor having at least two turns, and wherein the resonator coil includes a first pre-selected coupling point for coupling to a signal lead and a second pre-selected coupling point for coupling to a return lead, said coupling points being located on different turns.

5. The probe of claim 4 wherein the pre-selected coupling points define a turns ratio for the resonator coil, and wherein the resonator coil turns ratio is sufficient for the resonator coil to substantially match the transmission medium's characteristic impedance.

6. The probe of claim 5 wherein the resonator coil has a length of approximately 4⅛ inches.

7. The probe of claim 6 wherein the resonator coil turns ratio is approximately 5:1.

8. The probe of claim 4 wherein the resonator coil is substantially self-matching with the transmission medium's characteristic impedance such that the voltage standing wave ratio (VSWR) for the resonator coil is not greater than approximately 2:1.

9. The probe of claim 4 wherein the conductor is 30 gauge wire.

10. The probe of claim 4 wherein the conductor is 36 gauge wire.

11. The probe of claim 4 further comprising an insulating sheath within which the resonator coil is disposed.

12. The probe of claim 4 further comprising a processor coupled to a transmission medium, the transmission medium being connected to the resonator coil for receiving the resonator coil signal, and the processor being configured to process the resonator coil signal to generate therefrom an image of an interior portion of the body.

13. The probe of claim 4 wherein the resonator coil has a cross-sectional diameter in a range of approximately 0.25 mm to approximately 2 mm.

14. The probe of claim 13 wherein the resonator coil diameter is a range of approximately 1 mm to approximately 2 mm.

15. The probe of claim 14 wherein the resonator coil is an intravascular resonator coil.

16. The probe of claim 4 further comprising an intracorporeal catheter within which the resonator coil is disposed.

17. The probe of claim 16 wherein the catheter includes a channel for delivering a substance to an interior portion of the body.

18. An RF probe for use in analyzing an interior portion of a body, the probe comprising:
   a resonator coil comprising a conductor formed into an open winding having a first end and a second end, the winding having a plurality of turns;
   a transmission medium having a signal lead and a return lead, the signal lead being coupled to an intermediate point on the winding and the return lead being coupled to one of said first or second end of the resonator coil; and
   wherein the coupling between the transmission medium and the resonator coil defines a turns ratio for the resonator coil winding, the turns ratio being a ratio that substantially self-matches the resonator coil to a characteristic impedance of the transmission medium.

19. The probe of claim 18 wherein the resonator coil has a resonator length such that the resonator coil is substantially self-tuned to a desired resonant frequency.

20. The probe of claim 19 wherein the resonator coil has a cross-sectional diameter in a range of approximately 0.25 mm to approximately 2 mm.

21. The probe of claim 19 wherein the resonator coil is self-tuned to a resonant frequency of approximately the Larmour frequency.

22. The probe of claim 21 wherein the resonator coil length is approximately 4⅛ inches.

23. The probe of claim 22 wherein the resonator coil turns ratio is 5:1.

24. The probe of claim 19 wherein the resonator coil turns ratio is a ratio such that the resonator coil is substantially sell-matched to a transmission medium characteristic impedance of 50 Ω.

25. The probe of claim 24 wherein the resonator coil length is approximately 4⅛ inches.

26. The probe of claim 25 wherein the resonator coil turns ratio is 5:1.

27. The probe of claim 19 further comprising an insulating sheath surrounding the resonator coil.

28. The probe of claim 19 further comprising a catheter surrounding the resonator coil.

29. The probe of claim 1 wherein the resonator coil is an intravascular self-tuned resonator coil.

30. The probe of claim 1 wherein the resontator coil is an intravascular self-tuned resonator coil.

* * * * *